United States Patent [19]

Maeda et al.

[11] Patent Number: 4,950,814
[45] Date of Patent: Aug. 21, 1990

[54] LIQUID FLUOROCARBON AND A METHOD FOR PRODUCING THE SAME

[75] Inventors: Toshiyuki Maeda, Kadoma; Akihiro Mabuchi, Kyoto; Hiroyuki Fujimoto, Sakurai, all of Japan

[73] Assignee: Osaka Gas Company Limited, Japan

[21] Appl. No.: 427,419

[22] Filed: Oct. 26, 1989

[30] Foreign Application Priority Data

Oct. 26, 1988 [JP] Japan .................... 63-270342

[51] Int. Cl.$^5$ ............. C07C 17/02; C07C 17/33; C07C 19/08; C07C 23/18
[52] U.S. Cl. ................... 570/130; 570/131; 570/148; 228/42; 228/218
[58] Field of Search ........... 570/144, 147, 129, 130, 570/331, 148

[56] References Cited

U.S. PATENT DOCUMENTS

| | | | |
|---|---|---|---|
| 3,775,489 | 11/1973 | Margrave et al. | 260/648 F |
| 4,453,029 | 6/1984 | Lagow | 570/131 |
| 4,739,112 | 4/1988 | Saru | 570/130 |
| 4,777,304 | 10/1988 | Schweighardt et al. | 570/130 |
| 4,801,761 | 1/1989 | Bailey et al. | 570/130 |
| 4,827,053 | 5/1989 | Bailey et al. | 570/130 |
| 4,849,553 | 7/1989 | Bailey et al. | 570/130 |
| 4,873,315 | 10/1989 | Schweighardt et al. | 570/130 |

*Primary Examiner*—J. E. Evans
*Attorney, Agent, or Firm*—Sprung Horn Kramer & Woods

[57] ABSTRACT

Disclosed is a novel fluorocarbon comprising carbon atoms and fluorine atoms and having no double bond, the atomic ratio of fluorine to carbon atoms being 1.50 to 1.93, which exhibits a liquid state at room temperature. The liquid fluorocarbon has excellent water- and oil-repellent properties and can advantageously be used, for example, not only as a water- and oil-repellent but also as an inert liquid, a heat transfer agent and a vapor phase soldering liquid in various fields, especially in the electronic industry. The liquid fluorocarbon can be obtained directly from a pitch or from a pitch fluoride which can be obtained by direct fluorination of a pitch.

7 Claims, 24 Drawing Sheets

LIQUID FLUOROCARBON AND A METHOD FOR PRODUCING THE SAME

Background Of The Invention

1. Field Of The Invention

The present invention relates to a novel liquid fluorocarbon and a method for producing the same. More particularly, the present invention relates to a liquid fluorocarbon which is liquid at room temperature, differing not only from the conventional solid graphite fluoride obtained by directly fluorinating a carbon or graphite material, but also from the conventional solid pitch fluoride obtained by directly fluorinating a pitch, and also relates to the production thereof. The novel liquid fluorocarbon has excellent water- and oil-repellent properties.

2. Discussion Of Related Art

Recently, a graphite fluoride prepared by the direct fluorination of a carbon material having a relatively well developed graphite structure, such as natural graphite or heat-treated coke, has been attracting attention as a new industrial material because of its unique properties. For example, a poly-monocarbon monofluoride represented by formula $(CF)_n$ is well known as one of the graphite fluorides. $(CF)_n$ is a solid powder material having excellent lubricating and water- and oil-repellent properties as well as excellent chemical resistance. Therefore, $(CF)_n$ has been used as a solid lubricant, and also used as anti-wetting, stain-resistant and water- and oil-repellent materials. Further, $(CF)_n$ has been used as an active material capable of providing a primary cell of high energy density and long shelf life in which voltage drop due to discharge is substantially not observed for a long period of time as disclosed in U.S. Pat. Specification No. 3,536,532.

A poly-dicarbon monofluoride represented by formula $(C_2F)_n$ which was found by Watanabe et al. has almost the same properties as $(CF)_n$, and is highly appreciated in a wide variety of industrial fields (see, for example, U.S. reissued Pat. No. Re 30,667).

Further, a pitch fluoride which is solid at room temperature has been obtained by fluorinating a pitch (see for example, European Pat. Application Publication No. 0 222 149). The pitch fluoride has unique properties, for example, a property such that it is capable of forming a film by vacuum deposition, differing from the graphite fluoride.

The above-mentioned conventional graphite fluoride and pitch fluoride have excellent various properties as mentioned above. However, these conventional fluorides are solid at room temperature and, therefore, use thereof is restricted.

SUMMARY OF THE INVENTION

The present inventors have made further extensive and intensive studies with respect to the fluorination of a pitch. As a result, it has unexpectedly, surprisingly been found that a novel liquid fluorocarbon can be produced by the fluorination of a pitch under specific conditions or by the heat-treatment of a pitch fluoride in an atmosphere of fluorine under specific temperature conditions. This novel liquid fluorocarbon has not only excellent water- and oil-repellent properties alike the conventional graphite fluoride and pitch fluoride, but also a characteristic property that it is liquid at room temperature, differing from the conventional graphite fluoride and pitch fluoride which are solid at room temperature. Therefore, this novel liquid fluorocarbon can also be advantageously used as an inert liquid which is important, for example, in the field of the electronic industry. Based on the above findings, the present invention has been completed.

Accordingly, an object of the present invention is to provide a novel fluorocarbon which has excellent properties alike a pitch fluoride but which is liquid at room temperature, differing from the pitch fluoride.

Another object of the present invention is to provide a method for producing a novel liquid fluorocarbon in high yield.

The foregoing and other objects, features and advantages of the present invention will be apparent to those skilled in the art from the following detailed description taken in connection with the accompanying drawings.

Figure 1:
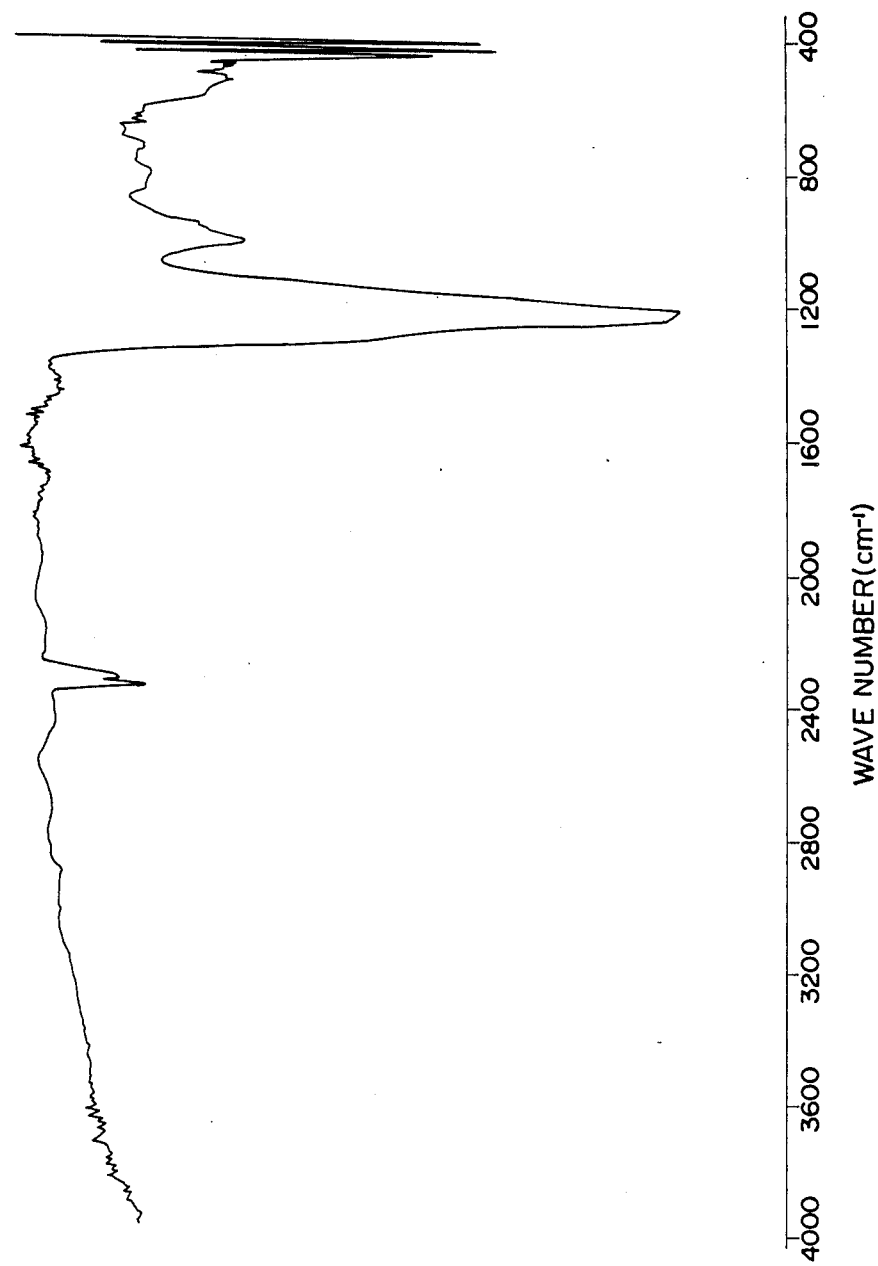
FIG. 1 shows the IR (infrared absorption) spectrum of a liquid fluorocarbon of the present invention obtained in Example 1 as described later.

According to the present invention, there is provided a liquid fluorocarbon comprising carbon atoms and fluorine atoms and having no double bond, the atomic ratio of fluorine to carbon atoms being 1.50 to 1.93, the liquid fluorocarbon exhibiting:

(a) in the infrared absorption spectrum, a peak at about 1215 $\pm 7$ cm$^{-1}$ having a maximum intensity, a peak at about 1025 $\pm 7$ cm$^{-1}$ having an intensity lower than that of the peak appearing at about 1215 $\pm 7$ cm$^{-1}$ and a peak at about 971 $\pm 7$ cm$^{-1}$ having an intensity lower than that of the peak appearing at about 1025 ±7cm$^{-1}$;

(b) a number average molecular weight of 680 to 950 as measured by the vapor pressure osmotic pressure method;

(c) in the thermogravimetric analysis and differential thermal analysis curves, an exothermic, weight decrease with the temperature elevation up to 420° C., wherein a 100% weight decrease is reached at 420° C.;

(d) a liquid state at room temperature; and (e) in the $^{19}$F-NMR spectrum as measured taking the CF$_3$ group of benzotrifluoride as a standard for chemical shift, two peaks respectively ascribed to CF$_3$CF- and CF$_3$CF$_2$- groups at chemical shifts within the range of from 0 to −30 ppm, a broad peak ascribed to a CF$_2$ group at a chemical shift within the range of from −30 to −90 ppm and a peak ascribed to a CF group at a chemical shift within the range of from −100 to −150 ppm.

As described later, the liquid fluorocarbon of the present invention can be obtained directly from a pitch or from a pitch fluoride which can be obtained by the direct fluorination of a pitch.

It is known that a pitch has a layer structure in which layers containing planar aromatic condensed rings are stacked to form a packing structure. The planar aromatic condensed rings are believed to be crosslinked by an aliphatic hydrocarbon residue, such as methylene [Carbon, Vol. 15, 17(1977)]. In this literature, the layer structure of a planar aromatic condensed ring is confirmed by the following method. The quinoline insoluble contents (QI) of a pitch are observed by means of a high resolution electron microscope to confirm the layer structure of the planar aromatic condensed ring. Further, through the observations using a high resolution electron microscope etc., it is found that the sizes of the planar molecules are about 6 to 15Å, which correspond to condensed ring compounds having a molecular weight of 150 to 800 or more. On the other hand, the molecular weight is also determined by the solvent extraction method and found to be 400 to 3,000 or more. From these facts, the author of the literature concludes that relatively small condensed ring compounds are crosslinked by methylene to form higher molecular weight compounds. Further confirmation of the presence of a methylene group by H-NMR analysis and $^{13}$C-NMR analysis is still in progress.

The term "pitch" as used in the present invention is intended to mean those having the above-mentioned structure. Representative examples of pitches include products obtained by subjecting petroleum heavy oil or coal heavy oil, such as a still residue of petroleum distillation, thermal decomposition residue of naphtha, ethylene bottoms, liquefied coal and coal tar, to distillation to remove low boiling components having boiling points lower than 200° C., and products obtained by subjecting the above-obtained low boiling components-free products to a further treatment, such as heat treatment and/or hydrogenation. Representative examples of pitches also include products obtained by subjecting petroleum heavy oil or coal heavy oil to a treatment, such as heat treatment and/or hydrogenation, and subjecting the treated oil to distillation to remove low boiling components having boiling points lower then 200° C. As representative examples of pitches, there may be mentioned an isotropic pitch, a mesophase pitch, a hydrogenated mesophase pitch, etc. Further, in the present invention, mesocarbon microbeads can also be employed as a pitch in the present invention. Mesocarbon microbeads can be obtained by distilling a petroleum heavy oil or coal heavy oil to remove low boiling components, subjecting the resultant residue to heat treatment to form mesophase spheres and collecting the mesophase spheres. Both the pitches and mesocarbon microbeads are hereinafter often referred to simply as "pitch". It has been established in the art that a pitch or mesocarbon microbeads are different from a coke or graphite in that a pitch or mesocarbon microbeads have an atomic ratio of carbon to hydrogen atoms (C/H ratio) of 3 or less whereas a coke or graphite has a C/H ratio of 8 or more.

With respect to the characteristic features of the liquid fluorocarbon of the present invention, an explanation will be given below, referring to FIGS. 1 to 24 of the accompanying drawings.

In FIGS. 1, 4, 7, 10, 13, 16, 19 and 22, there are shown the IR spectra of liquid fluorocarbons of the present invention obtained in Examples 1 to 8, respectively.

In FIGS. 2, 5, 8, 11, 14, 17, 20 and 23, there are shown TGA and DTA curves of liquid fluorocarbons of the present invention obtained in Examples 1 to 8, respectively.

In FIGS. 3, 6, 9, 12, 15, 18, 21 and 24, there are shown $^{19}$F-NMR spectra of liquid fluorocarbons of the present invention obtained in Examples 1 to 8, respectively.

As is apparent from FIGS. 1, 4, 7, 10, 13, 16, 19 and 22, the liquid fluorocarbons of the present invention exhibit, in IR spectra thereof, a peak at about 1215 ±7 cm$^{-1}$ having a maximum intensity, a peak at about 1025 ±7 cm$^{-1}$ having an intensity lower than that of the peak appearing at about 1215 ±7 cm$^{-1}$ and a peak at about 971 ±7 cm$^{-1}$ having an intensity lower than that of the peak appearing at about 1025 ±7 cm$^{-1}$.

As is apparent from FIGS. 2, 5, 8, 11, 14, 17, 20 and 23, the liquid fluorocarbons of the present invention exhibit, in thermogravimetric analysis and differential thermal analysis curves thereof, an exothermic, weight decrease with the temperature elevation up to 420° C., wherein a 100% weight decrease is reached at 420° C.

As is apparent from FIGS. 3, 6, 9, 12, 15, 18, 21 and 24, the liquid flurocarbons of the present invention exhibit, in $^{19}$F-NMR spectrum thereof as measured taking the CF$_3$ group of benzotrifluoride as a standard for chemical shift, two peaks respectively ascribed to CF$_3$CF- and CF$_3$CF$_2$- groups at chemical shifts within the range of from 0 to −30 ppm, a broad peak ascribed to a CF$_2$ group at a chemical shift within the range of from −30 to −90 ppm and a peak ascribed to a CF group at a chemical shift within the range of from −100 to −150 ppm.

Elementary analysis shows that the liquid fluorocarbon of the present invention is composed substantially of carbon atoms and fluorine atoms and that the F/C atomic ratio is within the range of about 1.50 to about 1.93 although it varies depending on the fluorination degree.

The liquid fluorocarbon of the present invention has no double bond, which can be confirmed from an IR spectrum. The IR spectrum of the liquid fluorocarbon of the present invention does not exhibit any peaks ascribed to a double bond within the range of 1500 to 1800 cm$^{-1}$.

The liquid fluorocarbon of the present invention is in liquid state at room temperature. The color of the liquid fluorocarbon of the present invention varies depending on the type of a pitch employed as raw material and the reaction temperature for the formation thereof. In general, however, the fluorocarbon of the present invention is a slightly yellowish or colorless, transparent liquid.

The liquid fluorocarbon of the present invention has a number average molecular weight ($\equiv n$) of 680 to 950 as measured by the vapor pressure osmotic pressure method.

The major distinct feature of the liquid fluorocarbon of the present invention from graphite fluorides and pitch fluorides resides in that it is in liquid state at room temperature.

The liquid fluorocarbon of the present invention, despite its liquid state, has properties, such as water-repellent and oil-repellent properties, which are comparable to those of graphite fluorides, such as $(CF)_n$ and $(C_2F)_n$, and pitch fluorides.

As methods for producing the liquid fluorocarbon of the present invention, there may be mentioned the following three methods:

Method (I) which comprises the steps of (1) reacting a pitch with fluorine at a reaction temperature of from about 0 to about 350° C in a reaction zone and (2) elevating the temperature of the reaction zone containing the resultant pitch fluoride and fluorine to and then maintaining the reaction zone at a temperature which is higher than the above-mentioned reaction temperature but not higher than about 550° C.;

Method (II) which comprises reacting a pitch with fluorine in an atmosphere of fluorine in a reaction zone while elevating the temperature of the reaction zone to a temperature within the range of from about 200° C. to about 550° C.; and Method (III) which comprises heat-treating a solid pitch fluoride in an atmosphere of fluorine in a heating zone while elevating the temperature of the heating zone to a temperature which is sufficient for converting the solid pitch fluoride to a liquid fluorocarbon, with the proviso that the elevated temperature is not higher than about 550° C.

Method (I) is described in detail hereinbelow. Method (I) comprises the steps of (1) forming a pitch fluoride from a pitch and fluorine, and (2) subjecting the resultant pitch fluoride to heat treatment in an atmosphere of fluorine with temperature elevation.

In step (1), a pitch is brought into direct contact with a fluorine gas in a reaction zone, thereby to form a solid pitch fluoride. The reaction temperature for forming a solid pitch fluoride varies depending on the type of the pitch employed, but is generally selected in the range of about 0 to about 350° C. However, when the fluorination is conducted at relatively high temperatures within the above range, carbon-carbon bonds in the pitch are likely to undergo cleavage and gas formation is increased so that the yield of a solid pitch fluoride is lowered. In order to produce the liquid fluorocarbon of the present invention in high yield by Method (I), it is required that the reaction in step (1) be performed so as to produce a solid pitch fluoride in high yield. Accordingly, the temperature for the fluorination reaction in step (1) is preferably in the range of from about 0 to about 200° C., more preferably in the range of from 0 to about 150° C. With respect to the reaction time, it is preferred that the reaction be conducted until the weight of the reaction product becomes about 1.8 times to about 3.1 times that of the starting pitch (i.e., until no peak is observed for the pitch on an X-ray diffraction pattern thereof). Further continuation of the reaction after the weight of the reaction product has become about 3.1 times that of the starting pitch, has no additional effect but only disadvantageously prolongs the reaction time.

After a pitch fluoride has been formed in step (1) in the above manner, in step (2), the temperature of the reaction zone containing the solid pitch fluoride and fluorine is elevated to a temperature which is higher than the reaction temperature in step (1) but not higher than 550° C., preferably not higher than 500° C. With respect to the temperature elevation in step (2), when the temperature elevation rate is too high, part of the solid pitch fluoride is likely to be exothermically decomposed, so that the yield of the desired liquid fluorocarbon becomes low, or the solid pitch fluoride is, occasionally, entirely decomposed to gases so that no desired liquid fluoride is obtained. Therefore, it is preferred that the temperature elevation rate be not higher than 5° C./minute. The temperature elevation rate is more preferably in the range of from 0.1° C./minute to 3° C./minute, most preferably in the range of from 0.1° C./minute to 1° C./minute. In step (2), after the temperature of the reaction zone has been elevated to the above-mentioned temperature, the temperature is maintained for a period of at least 30 minutes, preferably for a period of 30 minutes to 12 hours, thereby to obtain the desired liquid fluorocarbon. In step (2), when the above-mentioned temperature elevation rate is 1° C./minute or lower, the above maintenance of the reaction zone at the elevated temperature can be omitted, and simultaneously with the completion of the temperature elevation, the formation of the desired liquid fluorocarbon has already been attained. Further, it is noted that with respect to step (2), when the temperature to which the temperature of the reaction zone is elevated, is lower than 400° C., it is possible that a solid pitch fluoride is obtained as a by-product. In order to produce the desired liquid fluorocarbon selectively in high yield, it is preferred that the temperature be elevated to 400 to 550° C. in step (2).

The pressure of fluorine to be used in Method (I) is not critical and is generally in the range of 0.07 to 1.5 atm. In Method (I), a fluorine gas may be used as it is or may be used after diluted with an inert gas. Examples of inert gases which can be used for diluting fluorine, include argon, helium, neon, etc. The inert gas may be generally used in a ratio not higher than 95% by volume relative to the fluorine gas.

As a material for equipments to be used in association with the reaction vessel, there may be used any of copper, stainless steel, Monel metal, nickel, etc. Further, as a material for the reaction vessel, when the reaction temperature not higher than 150° C. is employed in step (1), there may be used any of stainless steel, Monel metal and nickel. On the other hand, when the reaction is effected at a temperature higher than 150° C. in step (1) and step (2), Monel metal is satisfactory as a material for the reaction vessel, but nickel is preferably employed from the viewpoint of corrosion resistance.

As described above, examples of pitches to be used in Method (I) of the present invention include products obtained by distilling petroleum heavy oil or coal heavy oil, such as a still residue of petroleum distillation, thermal decomposition residue of naphtha, ethylane bottoms, liquefied coal oil and coal tar, to remove low boiling components having boiling points lower than 200° C., and also include products obtained by subjecting the above-obtained substances to further treatment, such as heat treatment and hydrogenation. Examples of pitches also include products obtained by subjecting petroleum heavy oil or coal heavy oil to treatment such as heat treatment and/or hydrogenation and subjecting the treated oil to distillation to remove low boiling components having boiling points lower then 200° C. As representative examples of pitches, there may be mentioned an isotropic pitch, a mesophase pitch, a hydrogenated mesophase pitch, mesocarbon microbeads, etc. Isotropic pitches can be prepared by distillation of the above-described petroleum heavy oil or coal heavy oil to remove low boiling components having boiling points lower than 200° C. Mesophase pitches can be prepared by heating petroleum heavy oil, coal heavy oil or isotropic pitch in an atmosphere of nitrogen gas at 300 to 500° C. until the content of anisotropic components in the resultant pitch becomes 90% or more. The content of anisotropic components may be determined by the use of a polarizing microscope. The hydrogenated mesophase pitch can be prepared by adding a hydrogen donor, such as tetrahydroquinoline and hydrogenated aromatic hydrocarbon, to an isotropic pitch at an isotropic pitch/hydrogen donor weight ratio of 1:10 to 10:1 and reacting them with each other in an atmosphere of nitrogen gas at 300 to 500° C. for 1 minute to 1 hour. Mesocarbon microbeads can be prepared by a method which comprises distilling petroleum heavy oil or coal heavy oil to remove low boiling components, subjecting the resultant residue to heat treatment, then subjecting the heat-treated residue to extraction with, for example quinoline to remove quinoline-soluble components, and collecting the resultant mesophase spheres as an insoluble matter from the matrix.

Hereinbelow, Method (II) is described in detail. In Method (II), a pitch is subjected to direct fluorination in a fluorine atmosphere under specific temperature conditions, thereby producing the desired liquid fluorocarbon in high yield in one step. That is, in this method, a pitch is reacted with fluorine in an atmosphere of fluorine in a reaction zone while elevating the temperature of the reaction zone to a temperature (final heating temperature) within the range of from about 200° C. to about 550° C., referably within the range of from about 200° C. to about 500° C. The reaction is completed simultaneously with the elevation of temperature of the reaction zone to the above-mentioned final heating temperature. With respect to the temperature elevation in Method (II), when the temperature elevation rate is too high, part of the intermediately formed solid pitch fluoride is likely to be exothermically decomposed so that the yield of the desired liquid fluorocarbon becomes low, or the intermediately formed solid pitch fluoride is, occasionally, entirely decomposed to gases so that no desired liquid fluoride is obtained. Therefore, it is preferred that the temperature elevation rate be not higher than 5° C./minute. The temperature elevation rate is more preferably in the range of from 0.1° C./minute to 3° C./minute, most preferably in the range of from 0.1° C./minute to 1° C./minute. With respect to other reaction conditions in Method (II), such as a final heating temperature, a pitch as a starting material, a fluorine gas pressure and a reaction vessel, the same conditions as in Method (I) may apply.

Hereinbelow, Method (III) is described in detail. In Method (III), a solid pitch fluoride, which has been prepared separately, is heat-treated in an atmosphere of fluorine in a heating zone while elevating the temperature of said heating zone to a temperature which is sufficient for converting said solid pitch fluoride to a liquid fluorocarbon, with the proviso that the elevated temperature is not higher than about 550° C. As described above, a solid pitch fluoride can be efficiently produced in high yield by reacting a pitch with fluorine at a temperature of from about 0 to about 200° C., more preferably from about 0 to about 150° C. Therefore, the appropriate final heating temperature to which the temperature of the heating zone is elevated is from about 200° C. to about 550° C., preferably from about 200° C. to about 500° C. Method (III) corresponds to step (2) of Method (I).

When a pitch fluoride is introduced into a reaction vessel which has previously been elevated to a final heating temperature, decomposition of the pitch fluoride is likely to occur with the danger of explosion. Therefore, the gradual temperature elevation is important.

With respect to other reaction conditions in Method (III), such as a temperature elevation rate, a final heating temperature, a heating time, a fluorine pressure, a reaction vessel, the same conditions as in step (2) of Method (I) may apply.

A solid pitch fluoride to be employed as a raw material in Method (III) is a compound defined as follows. That is, the pitch fluoride is a solid compound comprising carbon atoms and fluorine atoms and having a structure in which layers containing fluorinated condensed cyclohexane rings are stacked to form a packing structure, the atomic ratio of fluorine to carbon atoms being 0.5 to 1.8, the pitch fluoride exhibiting:

(a) in the powder X-ray diffraction pattern, a peak having a maximum intensity at about 13° ($2\theta$), a peak at about 40° ($2\theta$) having an intensity lower than that of the peak appearing at about 13° ($2\theta$) and no peak on the low side of diffraction angle relative to 13° ($2\theta$);

(b) in the spectrum of electron spectroscopy for chemical analysis, a peak due to a CF group at about 290.0 ±1.0 eV and a peak due to a $CF_2$ group at about 292.5 ±0.9 eV, the intensity ratio of the peak due to the $CF_2$ group to the peak due to the CF being 0.15 to 1.5; and (c) a property that it is capable of forming a film by vacuum deposition.

The pitch fluoride as raw material has, in the powder X-ray diffraction pattern, a peak having a maximum intensity at about 13° ($2\theta$) and a peak at about 40° ($2\theta$) having an intensity lower than that of the peak appearing at about 13° ($2\theta$). In addition, the pitch fluoride has no peak on the low side of diffraction angle relative to 13° ($2\theta$) at which the peak having the maximum intensity appears. The interlayer spacing of the layer structure in the pitch fluoride is 6.8 ±1.0 Å, and the X-ray diffraction pattern of the pitch fluoride is similar to that of $(CF)_n$ which is a lamellar compound having an interlayer spacing of about 7.5 Å.

The pitch fluoride is characterized by exhibiting, in the ESCA spectrum, a peak at about 290.0 ±1.0 eV due to a CF group (monofluorocarbon group) and a peak at about 292.5 ±0.9 eV due to a $CF_2$ group (difluorocarbon group). This indicates that in the pitch fluoride, $CF_2$ groups are not merely peripheral groups but constitute one of the principal components of the pitch fluoride. Elementary analysis shows that the pitch fluoride is composed substantially of carbon and fluorine and the F/C atomic ratio is within the range of about 0.5 to about 1.8 although it varies depending on the fluorination degree.

The color of the pitch fluoride varies depending on the kind of a pitch employed as raw material and the degree of fluorination. For example, the pitch fluorides prepared from isotropic pitches and hydrogenated mesophase pitches are generally yellowish white or white. On the other hand, the color of the pitch fluorides prepared from mesocarbon microbeads is generally brown and changes from brown through yellowish white to white as the fluorination degree becomes large.

The thermal stability of pitch fluorides varies slightly depending on the kind of a pitch employed as raw material and the reaction conditions, such as reaction temperature, but, in general, when the pitch fluoride is heated at temperatures higher than the temperatures employed for the formation of the pitch fluoride (about 250 to about 600° C.) in air, nitrogen gas or inert gas such as argon, it decomposes to produce a solid fluoro compound. The solid fluoro compound produced by the thermal decomposition of a pitch fluoride is capable of forming a film on various substrates by vacuum deposition or sputtering.

When the pitch fluoride is heated at temperatures of about 250 to about 600° C. in vacuo, the thermal decomposition of the pitch fluoride and formation of a film due to the vacuum evaporation of the decomposition product occur simultaneously and, hence, a film can be directly produced from a pitch fluoride in one step.

The pitch fluoride has water-repellent and oil-repellent properties comparable to those of graphite fluorides, such as $(CF)_n$ and $(C_2F)_n$, and superior to those of Teflon.

The pitch fluoride can be prepared, for example, by directly fluorinating a pitch or mesocarbon microbeads in an atmosphere of a fluorine gas.

In producing a pitch fluoride by direct fluorination of a pitch or mesocarbon microbeads in an atmosphere of a fluorine gas, the reaction temperature is not critical, and the reaction proceeds even at a temperature of lower than 0° C. However, when the reaction temperature is lower than 0° C., it needs a long time to produce a pitch fluoride. On the other hand, when the reaction temperature is higher than 350° C., gaseous fluorocarbons, such as $CF_4$ and $C_2F_6$, are formed as by-products, causing the yield of the pitch fluoride to be lowered. Therefore, it is preferable that the reaction be effected at from about 0 to about 350° C., more preferably at from about 0 to about 200° C., most preferably at from about 0 to 150° C. Further, from the viewpoints of reaction time and reaction stability, it is preferred to conduct the reaction at a temperature lower than the softening temperature of the pitch. The reaction time is not particularly critical. However, the reaction is generally conducted until the weight of the reaction product becomes about 1.8 times to about 3.1 times that of the starting pitch (i.e., until no peak is observed for the pitch on an X-ray diffraction pattern thereof). Further continuation of the reaction after the weight of the reaction product has become about 3.1 times that of the starting pitch, has no additional effect but only disadvantageously prolongs the reaction time. The pressure of fluorine to be used in the fluorination of a pitch is not critical and is generally in the range of 0.07 to 1.5 atm. In producing a pitch fluoride, a fluorine gas may be used as it is or after diluted with an inert gas. Representative examples of inert gases which may be used for diluting fluorine include argon, helium, neon, etc. The inert gas may generally be used in a ratio not higher than 95% by volume relative to the fluorine gas. In the production of a pitch fluoride, as a material for equipments to be used in association with the reaction vessel, there may be used any of copper, stainless steel, Monel metal, nickel, etc. Further, as a material for the reaction vessel, when the reaction temperature not higher than 150° C. is employed, there may be used any of stainless steel, Monel metal and nickel. On the other hand, when the reaction is effected at a temperature higher than 150° C., Monel metal is satisfactorily used as a material for the reaction vessel but nickel is preferably employed from the viewpoint of corrosion resistance. With respect to the details of a pitch fluoride, reference may be made to, for example, European Pat. Application Publication No. 0 222 149.

In any of Methods (I) to (III) of the present invention, the temperature elevation may be conducted continuously or intermittently.

As mentioned above, the liquid fluorocarbon according to the present invention has water-repellent and oil-repellent properties, which are comparable to those of pitch fluorides and graphite fluorides, such as $(CF)_n$ and $(C_2F)_n$, but is liquid at room temperature, differing from the conventional pitch fluoride. Accordingly, the fluorocarbon of the present invention is useful, for example, not only as a water-and oil-repellent but also as an inert liquid, a heat transfer agent and a vapor phase soldering fluid which are important in various fields, especially in the electronic industry. Further, the liquid fluorocarbon of the present invention is advantageously used as a raw material for water-and oil-repellent thin films by virtue of characteristics such that when the liquid fluorocarbon is heated at about 100 to 200° C. in air, the fluorocarbon is solidified by volatilization of volatile components thereof.

[EXAMPLE]

This invention will now be described in more detail with reference to the following examples which by no means should be construed to be limiting the scope of the present invention.

In the present specification and the following examples, various analyses were carried out by the following methods.

(1) Thermogravimetric analysis (TGA) and differential thermal analysis (DTA)

Measured in an atmosphere of argon gas (at a flow rate of 50 cc/min) using a thermal analyzer DT-40 manufactured and sold by Shimadzu Corporation, Japan.

(2) Measurement of number average molecular weight

Apparatus : 117 type Corona molecular weight measuring apparatus manufactured and sold by Corona Denki K.K., Japan.
Temperature : 28° C.
Solvent : 1,1,2-trichloro-1,2,2-trifluoroethane.
Standard substance : benzyl (molecular weight: 210.23).

With respect to the vapor pressure osmotic pressure method, reference may be made to "Kiki Bunseki no Tebiki 2 (Handbook of Analysis by Apparatus and Equipment, No. 2)", pp 82 (1984), published by Kagaku Dojin, Japan.

(3) Infrared ray absorption spectrum

Measured by means of 60 SX type FT-IR spectrometer manufactured and sold by Nicolet Co., Ltd., U.S.A.

(4) $^{19}$F-NMR spectrum

Apparatus: JNM-GX270 manufactured and sold by JEOL, LTD., Japan.

Measurement is carried out using benzene hexafluoride as a solvent or without using a solvent, and the $CF_3$ group of benzotrifluoride is taken as a standard (zero ppm) for chemical shift.

(5) Elementary analysis

Carbon, hydrogen and nitrogen: Conducted using a CHN recorder MT-3 (manufactured and sold by Yanagimoto Seisakusho, Japan).

Fluorine: Conducted by Oxygen-Flask method under conditions described in the Journal "Japan Analyst 467 –473, Vol. 20(1971)".

(6) QI (quinoline insoluble fraction) of a pitch:

Measured according to JIS (Japanese Industrial Standards)-K2425.

(7) BI (benzene insoluble fraction) of a pitch:

Measured according to JIS-K2425 except that benzene is used instead of toluene.

Example 1

1 g of a hydrogenated mesophase pitch having the composition shown in Table 1 was placed in a reaction vessel made of nickel.

TABLE 1

| C content (% by weight) | H content (% by weight) | N content (% by weight) | BI (%) | QI (%) | ST[1] (°C.) |
|---|---|---|---|---|---|
| 95.08 | 3.88 | 0.75 | 93.87 | 17.94 | 303.4 |

[1]ST means a softening temperature.

The inside of the reaction vessel was evacuated and, then, filled with an argon gas until the internal pressure thereof reached an atmospheric pressure. Thereafter, a fluorine gas was flowed into the inside of the reaction vessel for 10 hours at a flow rate of 6 cc/min while maintaining the temperature in the reaction vessel at 70° C. (first step). The temperature was elevated to 550° C. at a temperature elevation rate of 1° C./min, and this temperature was then kept for 12 hours (second step). Thus, there was obtained 2.4 g of a liquid fluorocarbon. Elementary analysis showed that the F/C atomic ratio of the liquid fluorocarbon was 1.74. The number average molecular weight of the liquid fluorocarbon was 815 ±40.

Figure 2:
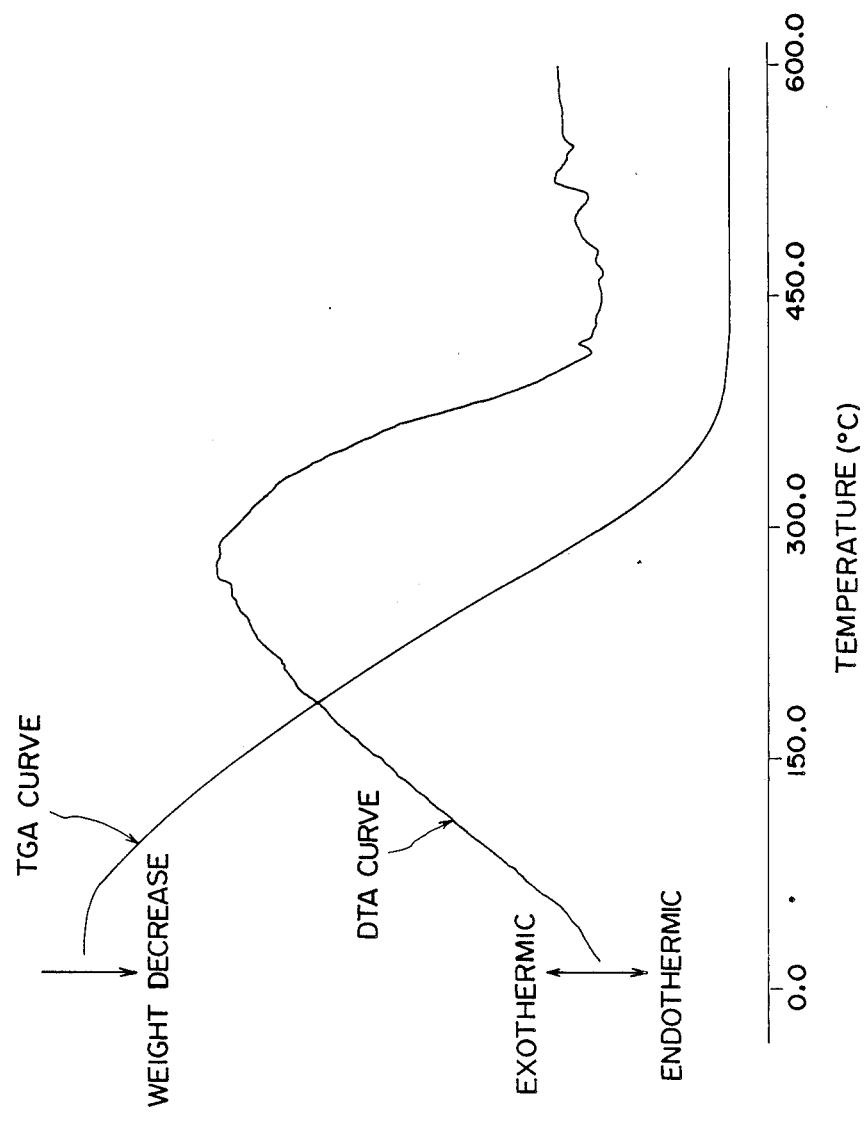
FIG. 2 shows the TGA (thermogravimetric analysis) and DTA (differential thermal analysis) curves of a liquid fluorocarbon of the present invention obtained in Example 1 as described later.
Figure 3:
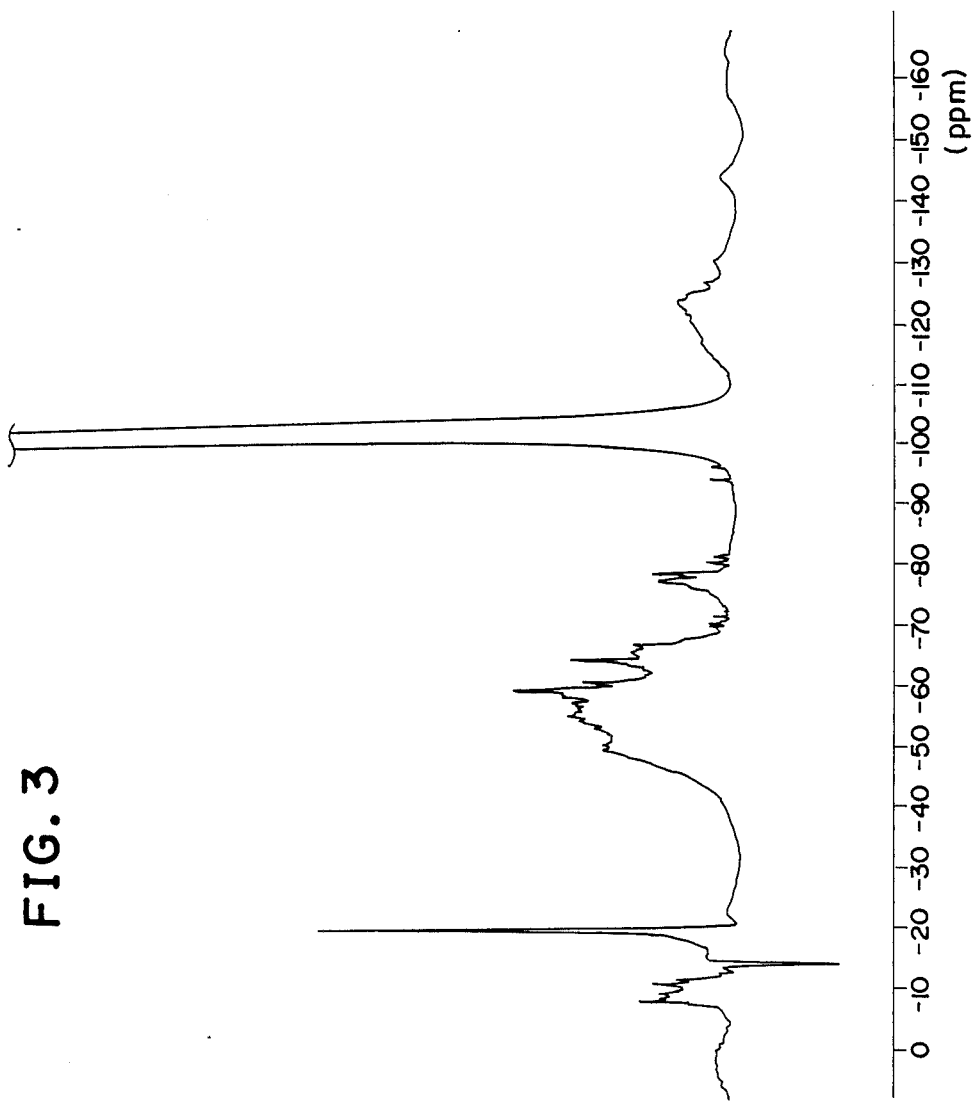
FIG. 3 shows the $^{19}F$-NMR (nuclear magnetic resonance) spectrum of a liquid fluorocarbon of the present invention obtained in Example 1 as described later.

The IR spectrum, TGA and DTA curves and $^{19}$F-NMR spectrum of the above-obtained liquid fluorocarbon are shown in FIGS. 1, 2 and 3, respectively.

Example 2

Figure 4:
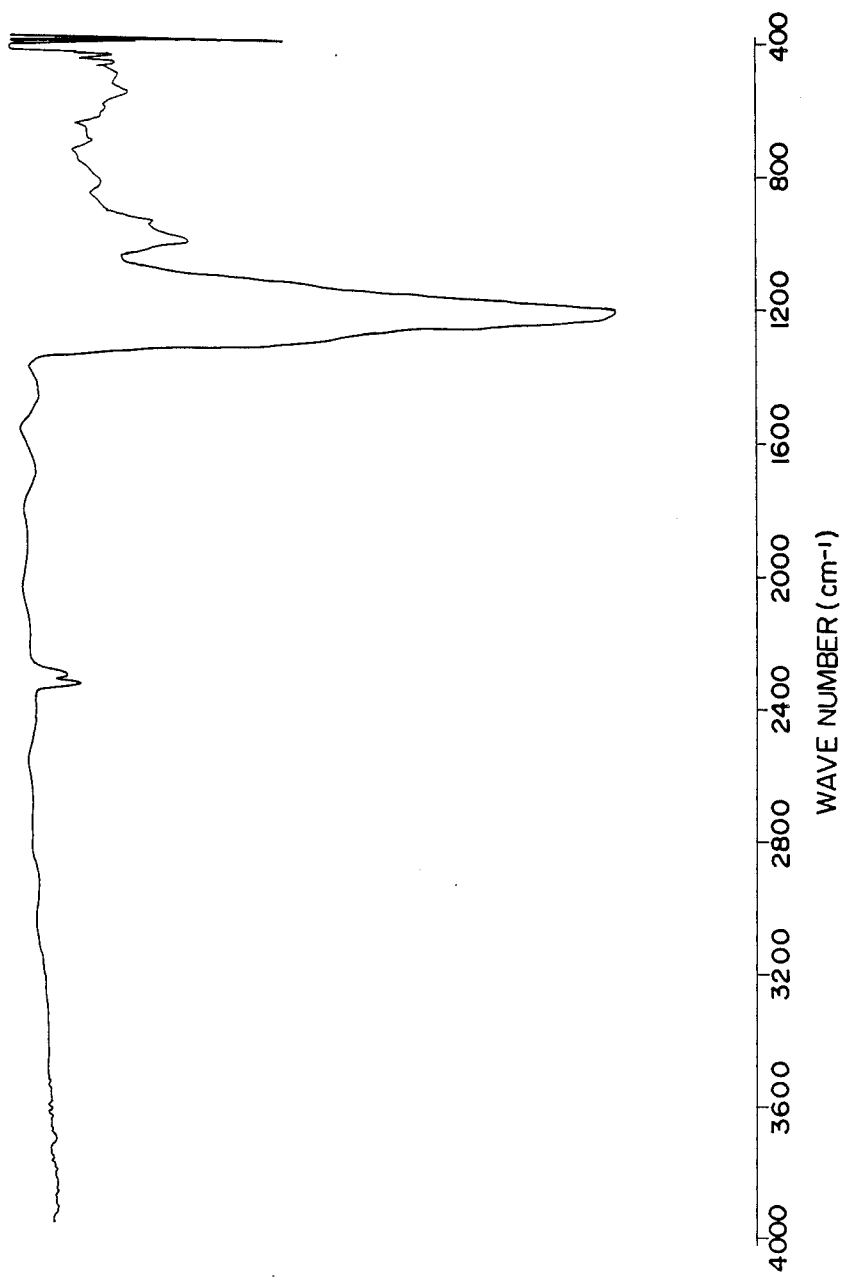
FIGS. 4, 5 and 6, respectively, show the IR spectrum, TGA and DTA curves and $^{19}F$-NMR spectrum of a liquid fluorocarbon of the present invention obtained in Example 2 as described later.
Figure 5:
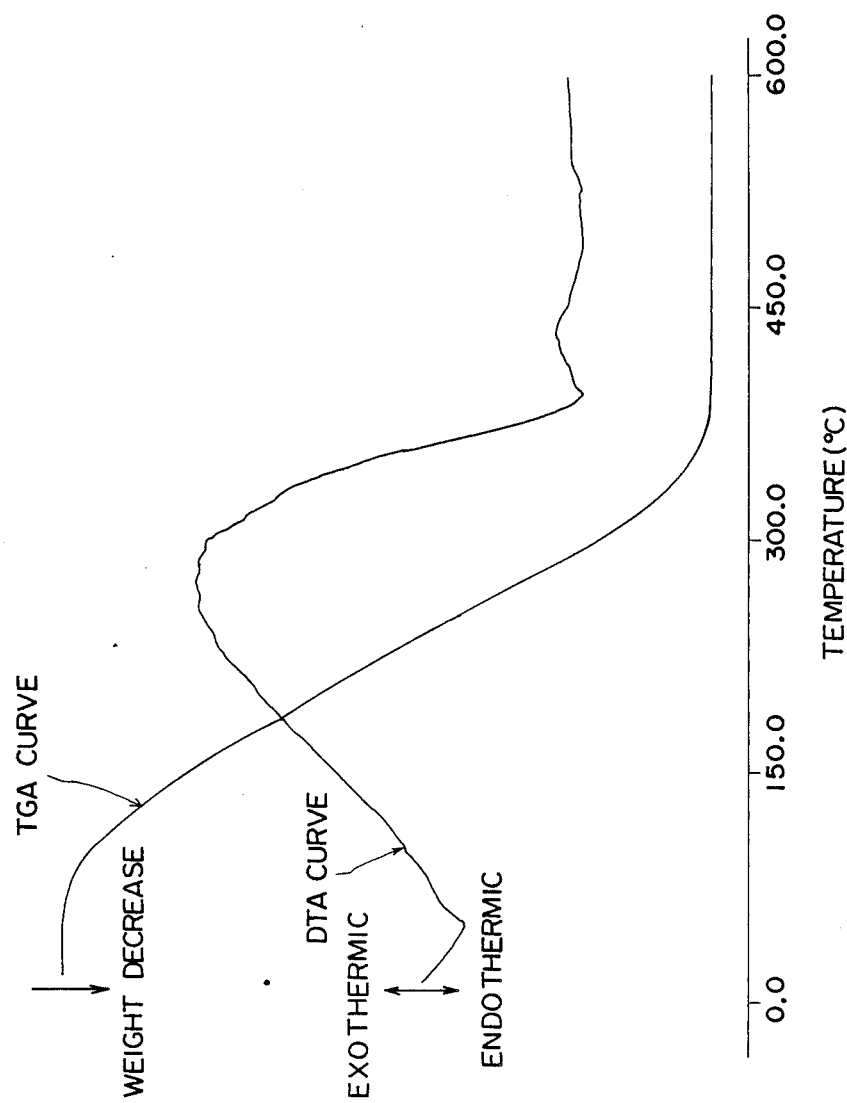
Figure 6:
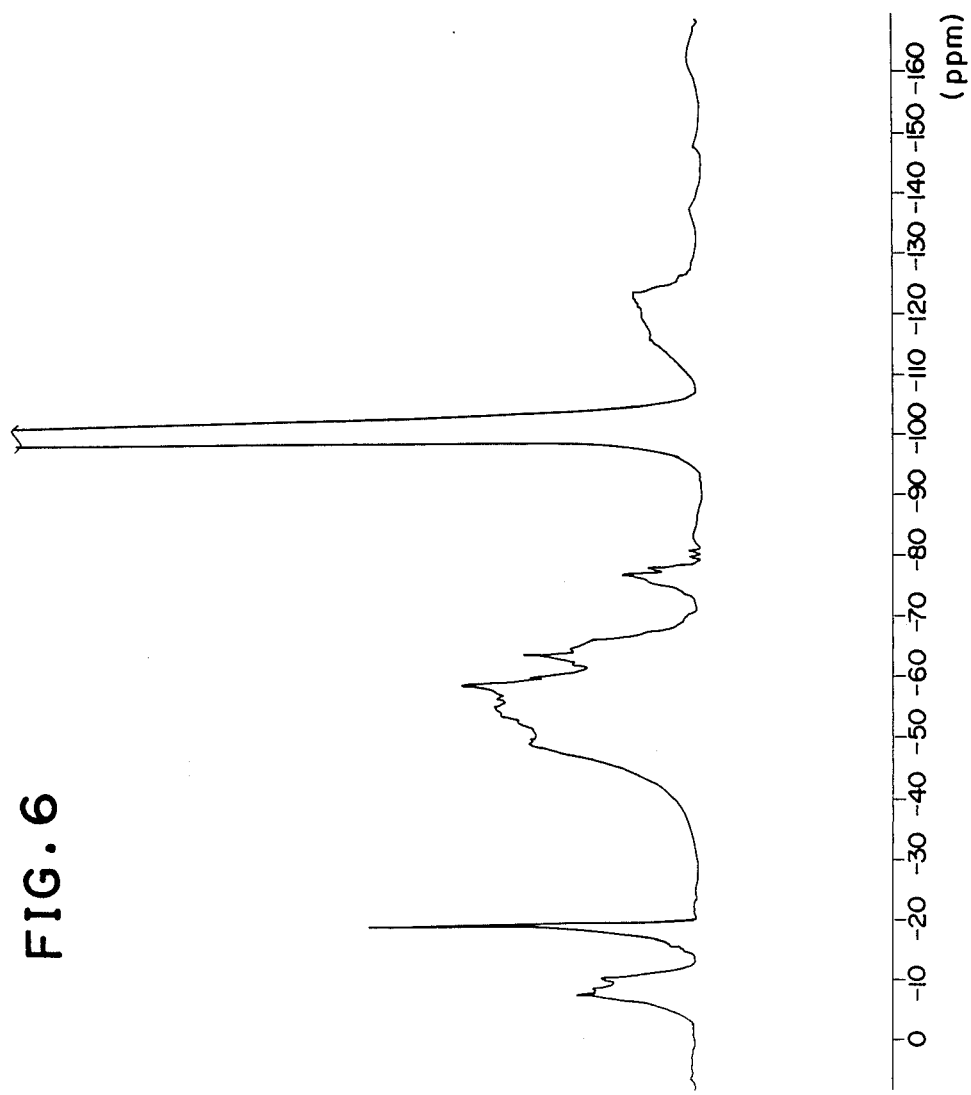

Substantially the same procedure as in Example 1 was repeated except that the reaction temperature of the second step was changed from 550° C. to 400° C., to obtain 1.64 g of a liquid fluorocarbon. The fluorocarbon has an F/C atomic ratio of 1.79 and a number average molecular weight of 856 ±40. The IR spectrum, TGA and DTA curves and $^{19}$F-NMR spectrum of the above-obtained liquid fluorocarbon are shown in FIGS. 4, 5 and 6, respectively

Reference Example

To a coal tar pitch (QI=0%) was added an equivolume of a hydrogenated anthracene oil. The resultant mixture was heated up to 450° C. at a temperature elevation rate of 15° C./min and then heated in an atmosphere of nitrogen gas at 450° C. for 1 hour, to thereby obtain a hydrogenated mesophase pitch. The obtained hydrogenated mesophase pitch had a QI content of 17.94%, a BI content of 93.87% and a softening temparature (ST) of 303.4° C. The hydrogenated mesophase pitch was subjected to elementary analysis. The results were as follows.

C 95.08%; H : 3.88%; N : 0.75%.

1 g of the above obtained hydrogenated mesophase pitch was placed in a 500 ml sealed-type cylindrical reaction vessel made of nickel (equipped with a jacket). The inside of the reaction vessel was evacuated, and then an argon gas was introduced thereinto until the internal pressure in the reaction vessel reached an atmospheric pressure. A fluorine gas was then flowed into the reaction vessel at a flow rate of 6 cc/min for 10 hours while maintaining the temperature at 70° C., to thereby obtain 2.9 g of a yellowish white pitch fluoride. Elementary analysis of the obtained yellowish white pitch fluoride showed that the F content, C content and F/C atomic ratio of the pitch fluoride were 68.21%, 32.35% and 1.33, respectively.

Example 3

2.9 g of the pitch fluoride obtained in the above Reference Example was placed in a sealed-type reaction vessel made of nickel. The inside of the reaction vessel was evacuated, and then a fluorine gas was flowed into the reaction vessel at a flow rate of 6 cc/min at 70° C. until the internal pressure of the reaction vessel reached an atmospheric pressure. The temperature in the reaction vessel was elevated to 200° C. at a temperature elevation rate of 1° C./min. Thereafter, the reaction vessel was cooled to room temperature, and the inside of the reaction vessel was evacuated to obtain 0.2 g of a liquid fluorocarbon. The F/C atomic ratio and number average molecular weight of the liquid fluorocarbon were 1.91 and 722 ±40, respectively.

Figure 7:
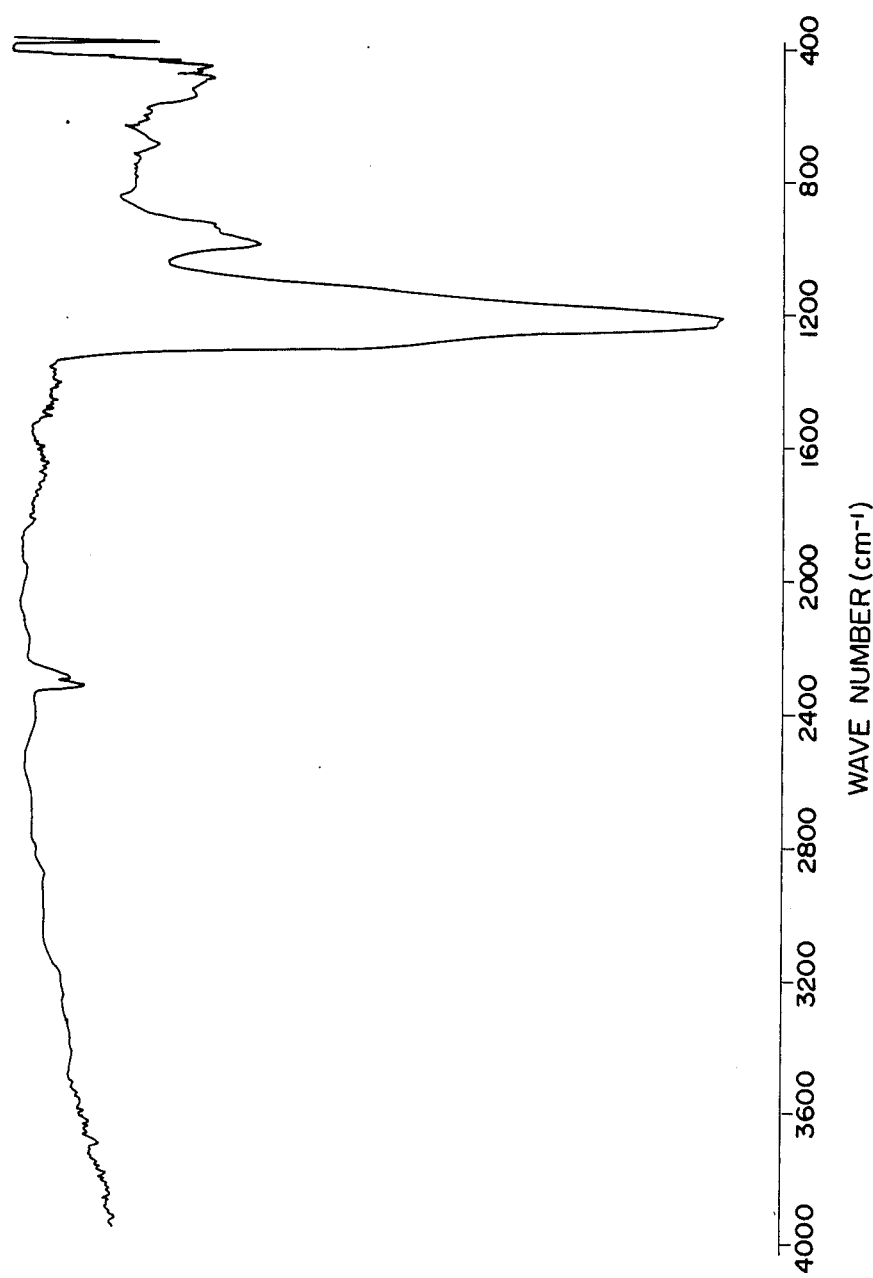
FIGS. 7, 8 and 9, respectively, show the IR spectrum, TGA and DTA curves and $^{19}F$-NMR spectrum of a liquid fluorocarbon of the present invention obtained in Example 3 as described later.
Figure 8:
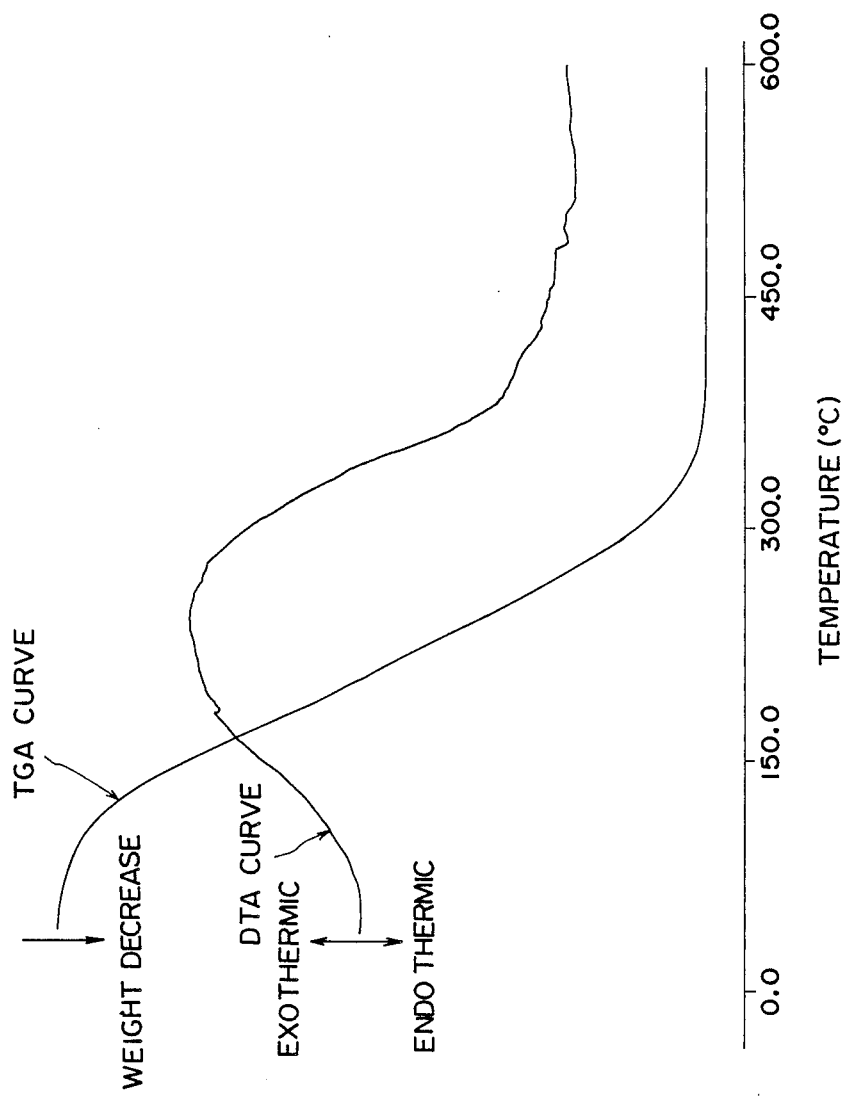
Figure 9:
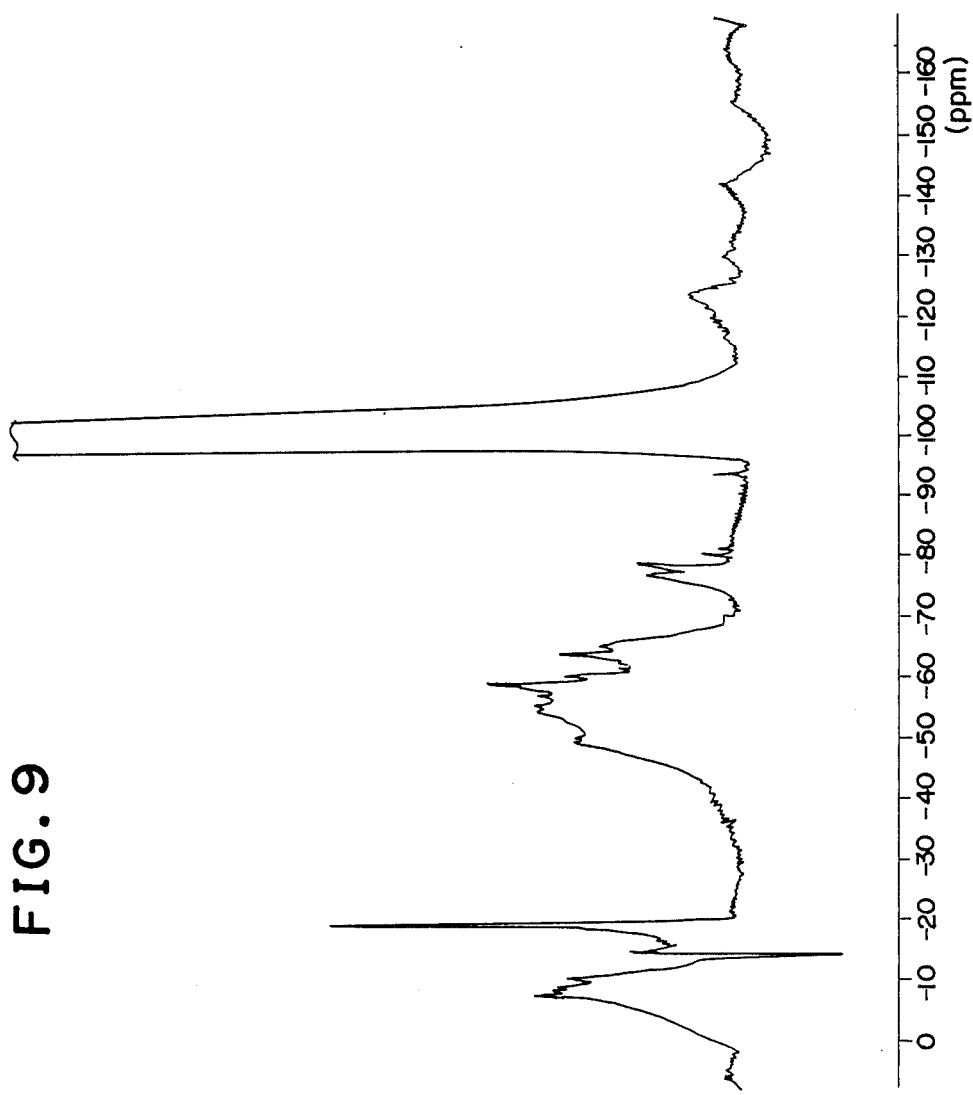

The IR spectrum, TGA and DTA curves and $^{19}$F-NMR spectrum of the obtained liquid fluorocarbon are shown in FIGS. 7, 8 and 9, respectively.

Example 4

Substantially the same procedure as in Example 1 was repeated except that an isotropic pitch having properties shown in Table 2 was used.

TABLE 2

| C content (% by weight) | H content (% by weight) | N content (% by weight) | BI (%) | QI (%) | ST (°C.) |
|---|---|---|---|---|---|
| 94.74 | 4.41 | 1.07 | 37.8 | 1.4 | 168.6 |

Figure 10:
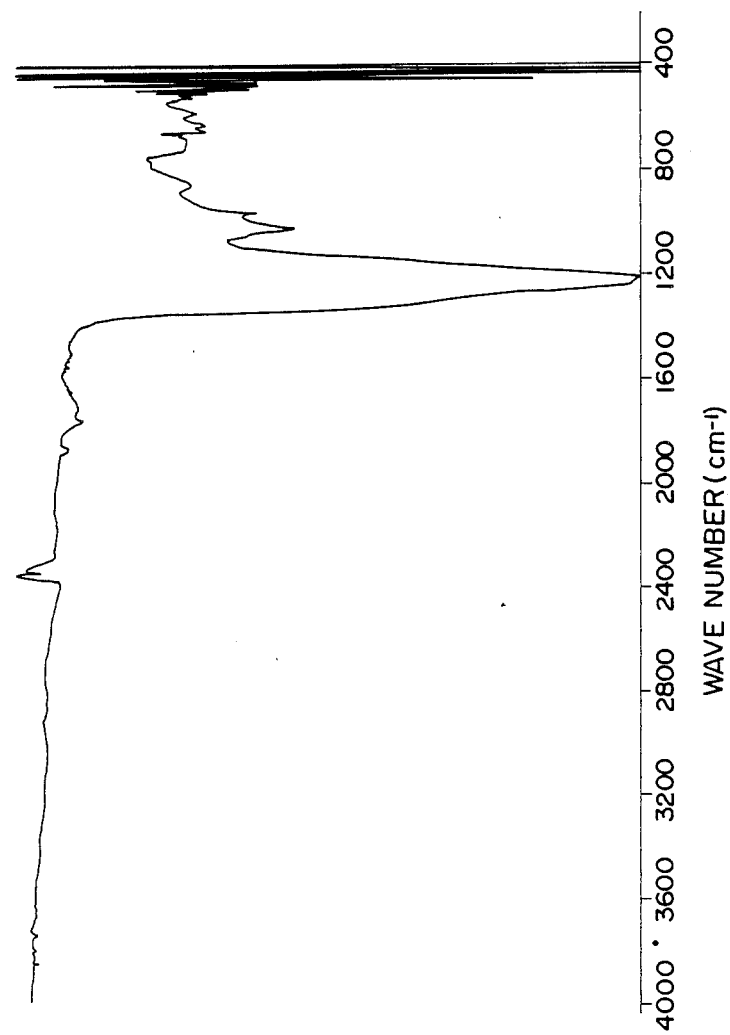
FIGS. 10, 11 and 12, respectively, show the IR spectrum, TGA and DTA curves and $^{19}F$-NMR spectrum of a liquid fluorocarbon of the present invention obtained in Example 4 as described later.
Figure 11:
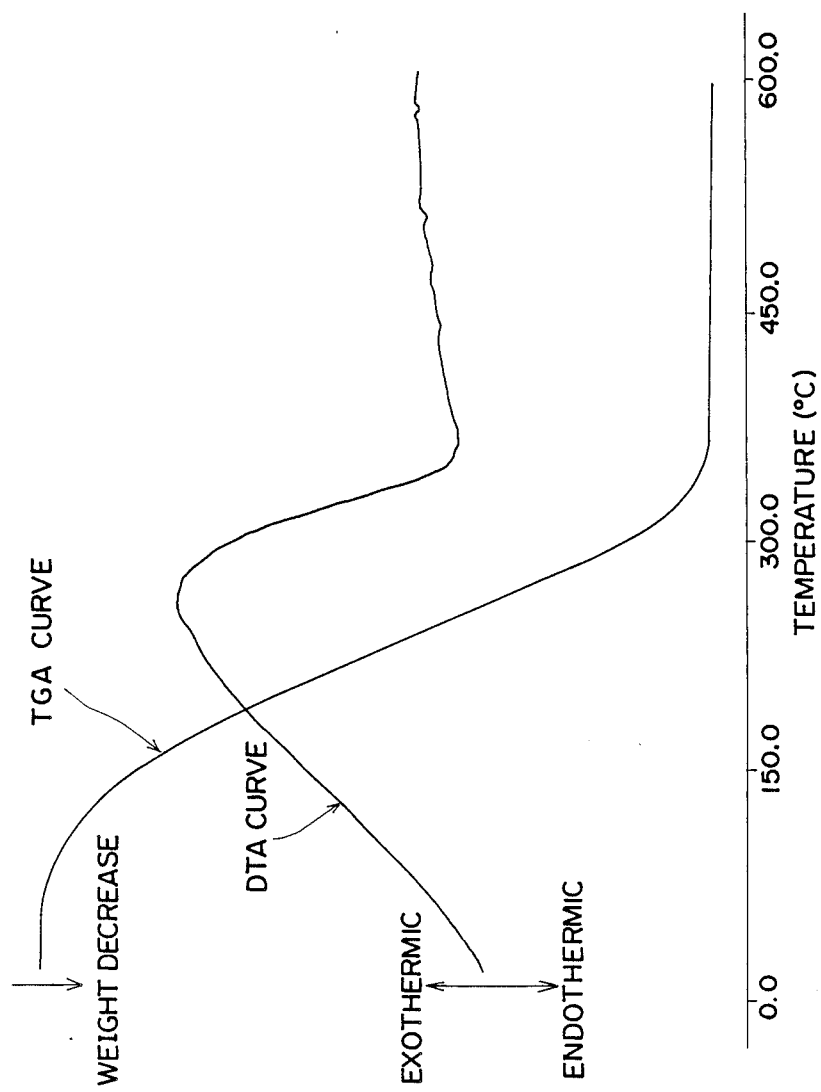
Figure 12:
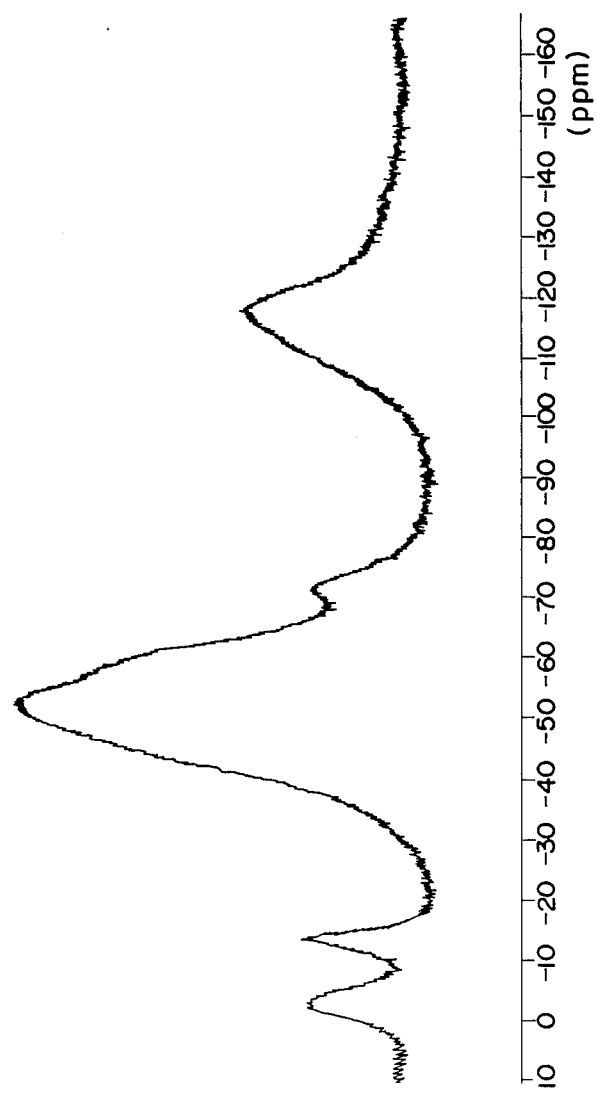

The reaction temperature of the second step was changed from 550° C. to 400° C. Thus, 0.66 g of a liquid fluorocarbon having an F/C atomic ratio of 1.50 was obtained. The number average molecular weight of the liquid fluorocarbon was 775 ±40. The IR spectrum, TGA and DTA curves and $^{19}$F-NMR spectrum (measured without dissolving in a solvent) of the liquid fluorocarbon are shown in FIGS. 10, 11 and 12, respectively.

Example 5

Substantially the same procedure as in Example 1 was repeated except that a petroleum pitch having composition shown in Table 3 was used.

TABLE 3

| C content (% by weight) | H content (% by weight) | N content (% by weight) | BI (%) | QI (%) | ST (°C.) |
|---|---|---|---|---|---|
| 87.21 | 6.17 | 1.75 | 48.9 | 19.0 | 239.8 |

Figure 13:
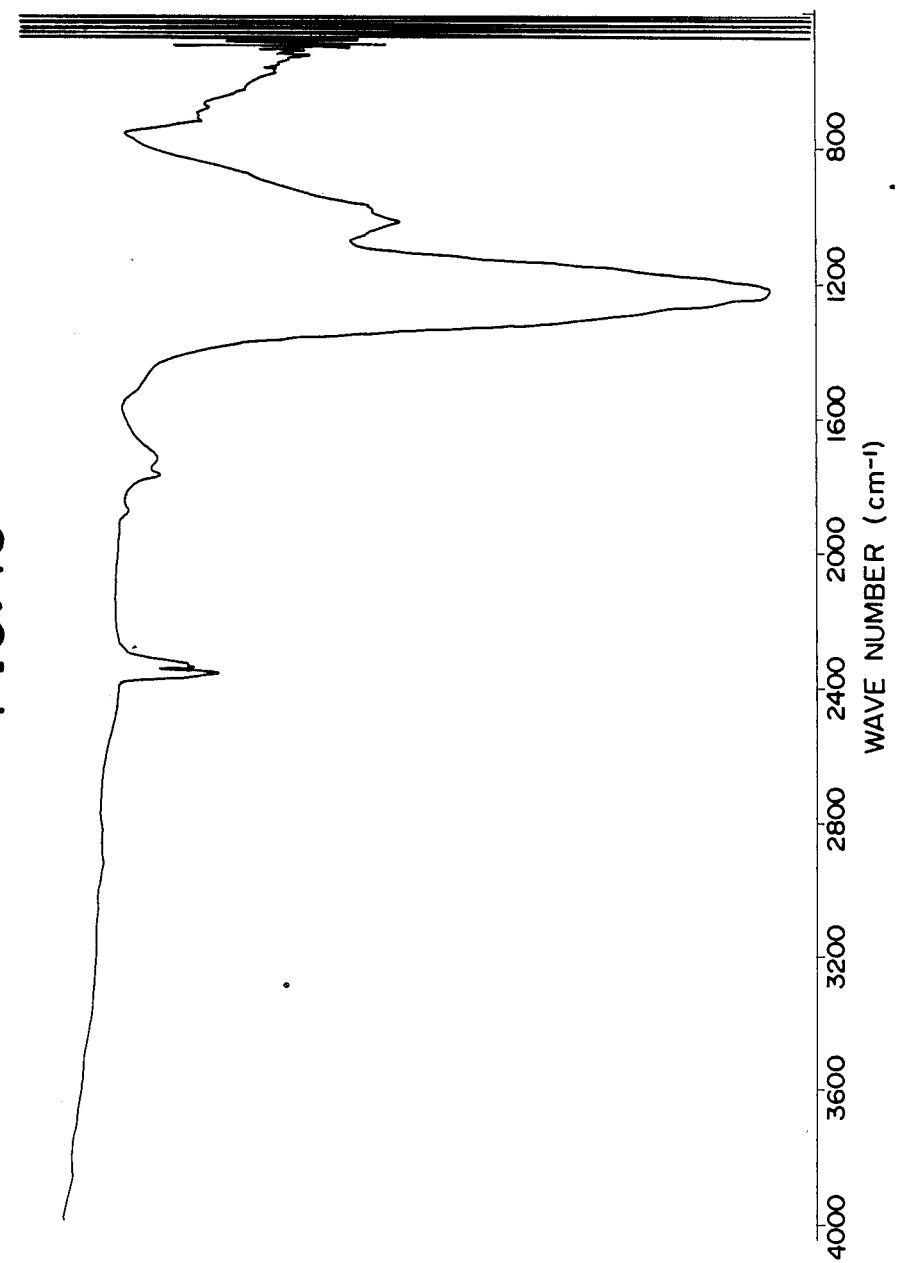
FIGS. 13, 14 and 15, respectively, show the IR spectrum, TGA and DTA curves and $^{19}F$-NMR spectrum of a liquid fluorocarbon of the present invention obtained in Example 5 as described later.
Figure 14:
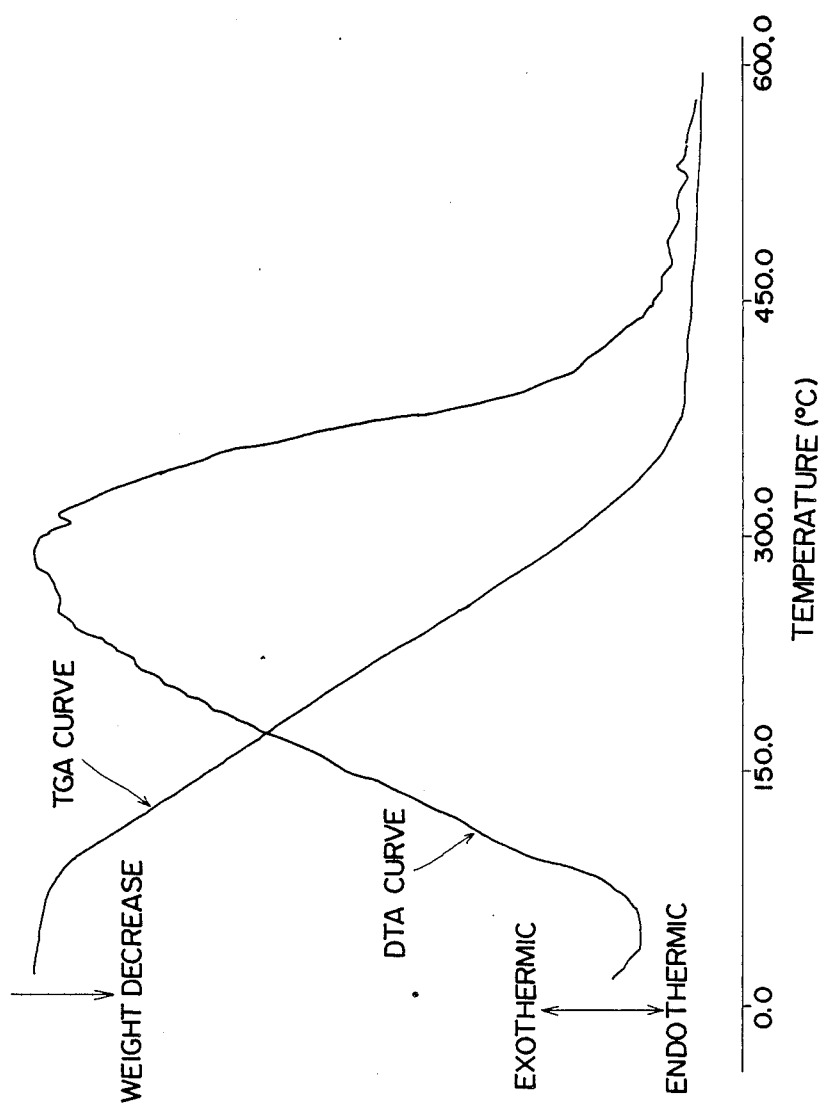
Figure 15:
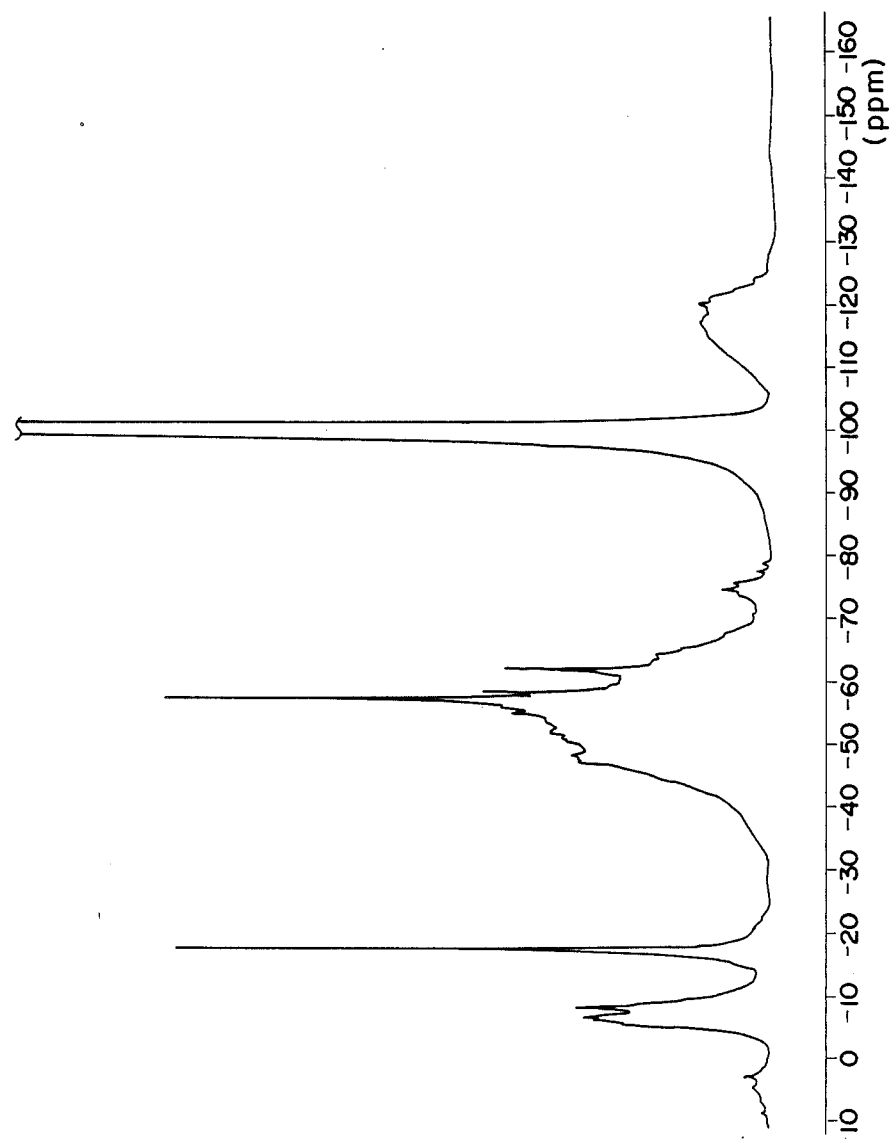

The reaction temperature of the first step was changed to 50° C. from 70° C. and the reaction temperature of the second step was changed to 400° C. from 550° C., to thereby obtain 0.42 g of a liquid fluorocarbon. The F/C atomic ratio and number average molecular weight of the liquid fluorocarbon were 1.56 and 893 ±40, respectively. The IR spectrum, TGA and DTA curves and $^{19}$F-NMR of the obtained liquid fluorocarbon are shown in FIGS. 13, 14 and 15, respectively.

Example 6

Figure 16:
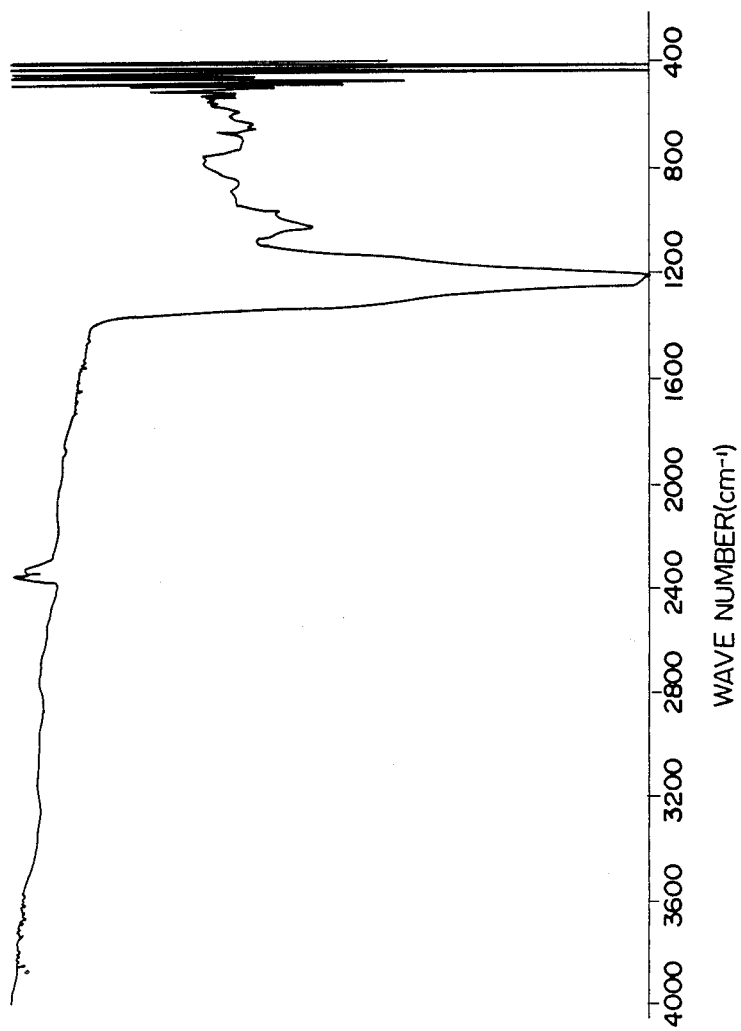
FIGS. 16, 17 and 18, respectively, show the IR spectrum, TGA and DTA curves and $^{19}F$-NMR spectrum of a liquid fluorocarbon of the present invention obtained in Example 6 as described later.
Figure 17:
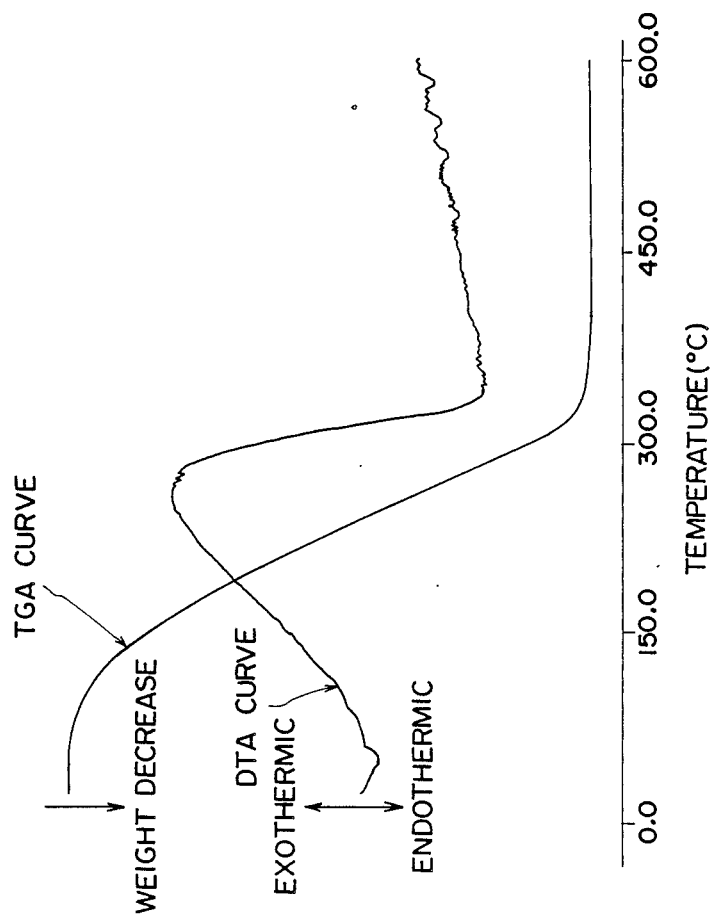
Figure 18:
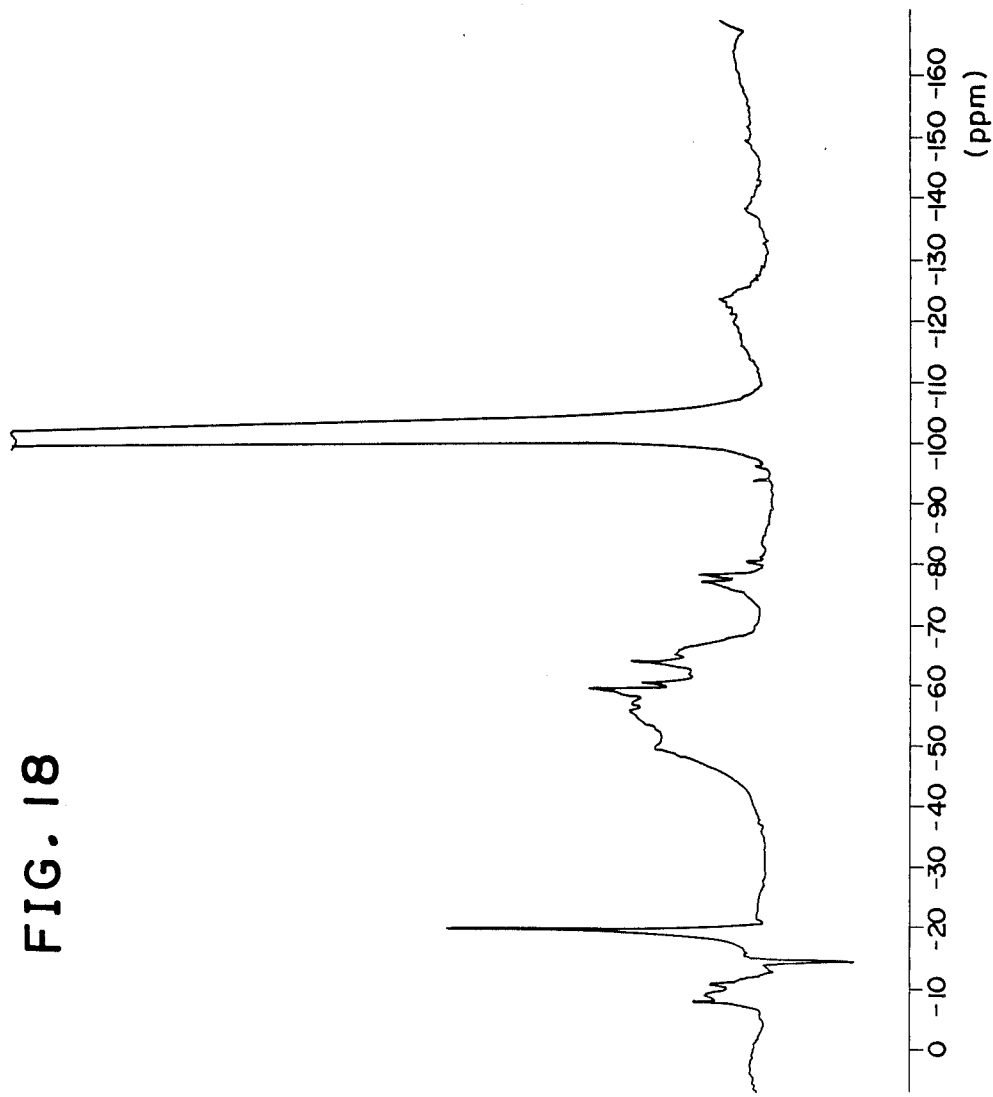

1 g of the same hydrogenated mesophase pitch as used in Example 1 was placed in a reaction vessel made of nickel. The inside of the reaction vessel was evacuated and, then, filled with an argon gas at room temperature until the internal pressure thereof reached an atmospheric pressure. Then, the temperature was elevated to 300° C. at a temperature elevation rate of 1° C./min while flowing fluorine gas into the reaction vessel at a flow rate of 6 cc/min. Thereafter, the reaction vessel was cooled to room temperature and the inside of the reaction vessel was evacuated. Thus, 0.8 g of a liquid fluorocarbon was obtained. Elementary analysis showed that the F/C atomic ratio and number average molecular weight of the liquid fluorocarbon were 1.70 and 720 ±40, respectively. The IR spectrum, TGA and DTA curves and $^{19}$F-NMR spectrum of the obtained liquid fluorocarbon are shown in FIGS. 16, 17 and 18, respectively.

Example 7

1 g of mesocarbon microbeads having the composition shown in Table 4 was placed in a reaction vessel made of nickel.

TABLE 4

| C content (% by weight) | H content (% by weight) | N content (% by weight) | BI (%) | QI (%) | ST (°C.) |
|---|---|---|---|---|---|
| 94.08 | 4.45 | 1.13 | 35.5 | 2.9 | 178.5 |

Figure 19:
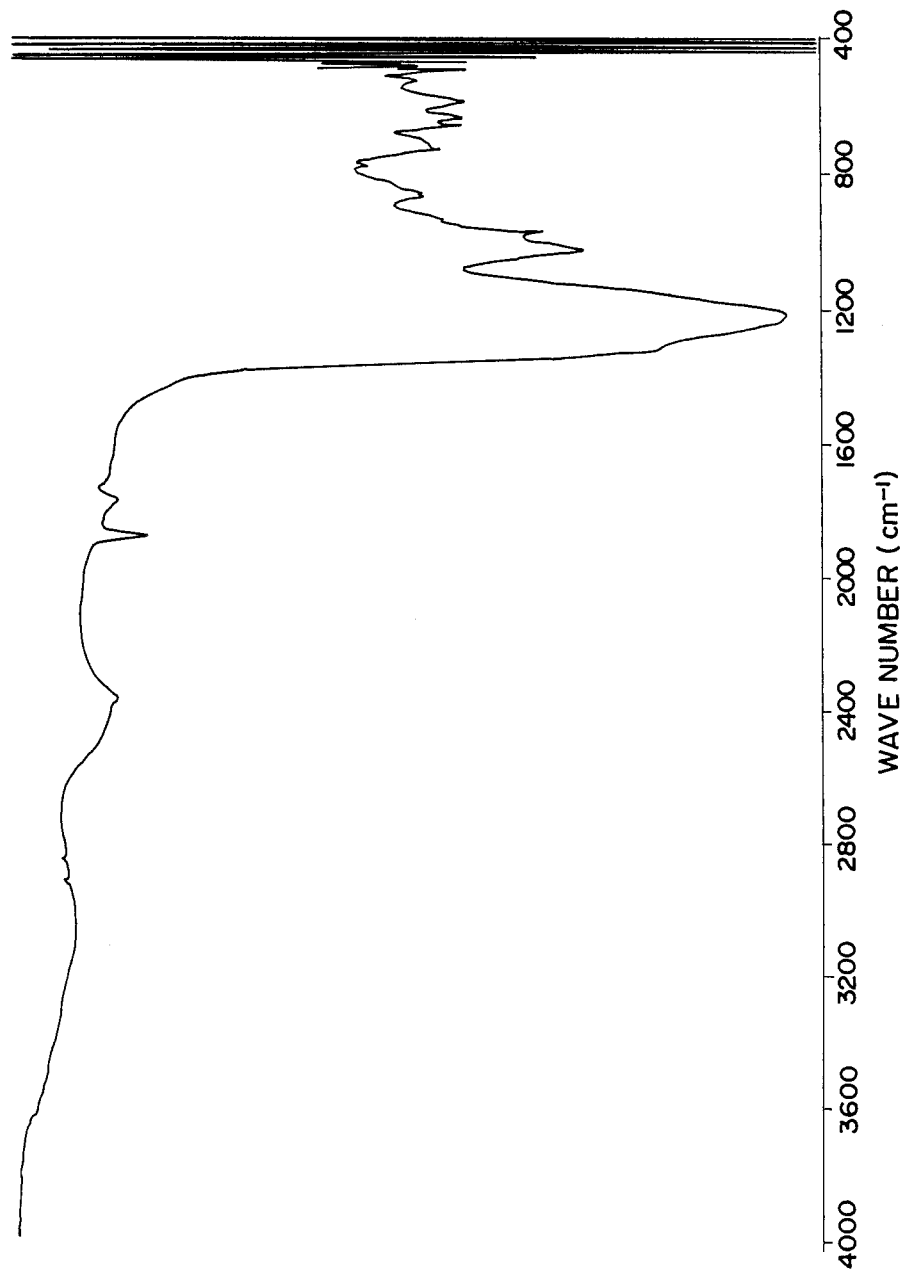
FIGS. 19, 20 and 21, respectively, show the IR spectrum, TGA and DTA curves and $^{19}F$-NMR spectrum of a liquid fluorocarbon of the present invention obtained in Example 7 as described later.
Figure 20:
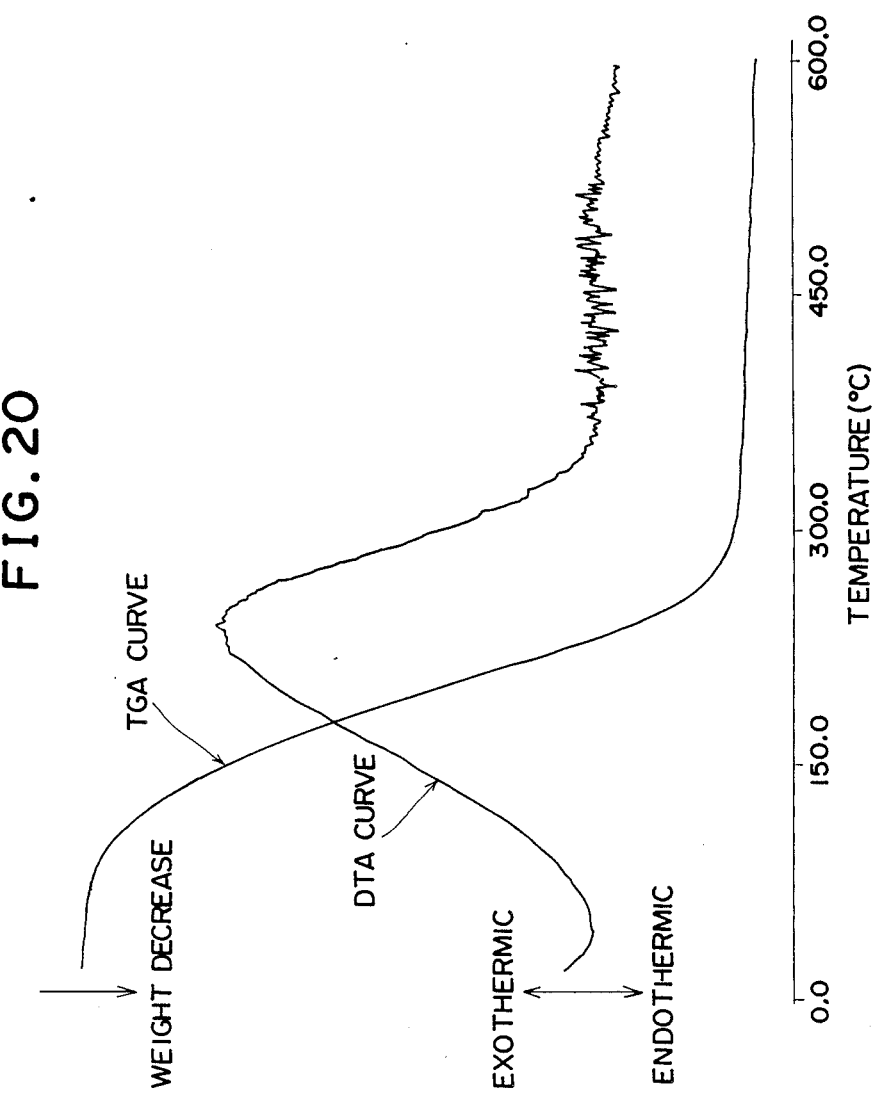
Figure 21:
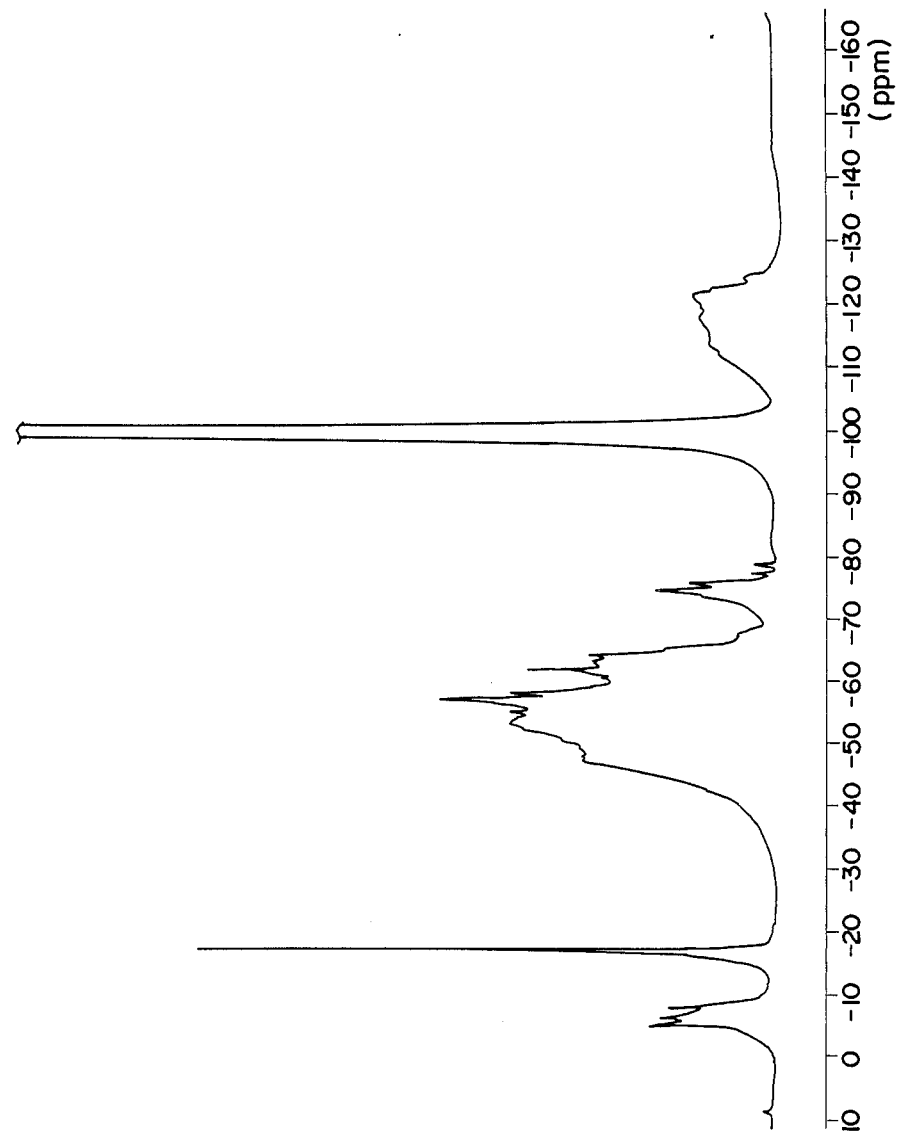

The inside of the reaction vessel was evacuated and, then, filled with an argon gas until the pressure in the reaction vessel reached an atmospheric pressure. A fluorine gas was then flowed into the reaction vessel at a flow rate of 6 cc/min for 10 hours while maintaining the temperature in the reaction vessel at 70° C. (first step). Thereafter, the temperature was elevated up to 300° C. at a temperature elevator rate of 1° C./min, and this temperature was then kept for 12 hours (second step), to thereby obtain 0.22g of a liquid fluorocarbon. The F/C atomic ratio and number average molecular weight of the liquid fluorocarbon were 1.50 and 725 ±40, respectively. The IR spectrum, TGA and DTA curves and $^{19}$F-NMR spectrum of the liquid fluorocarbon are shown in FIGS. 19, 20 and 21, respectively.

Example 8

1 g of mesocarbon microbeads having the composition shown in Table 5 was placed in a reaction vessel made of nickel.

TABLE 5

| C content (% by weight) | H content (% by weight) | N content (% by weight) | BI (%) | QI (%) | ST (°C.) |
|---|---|---|---|---|---|
| 94.02 | 3.21 | 0.88 | — | — | — |

Figure 22:
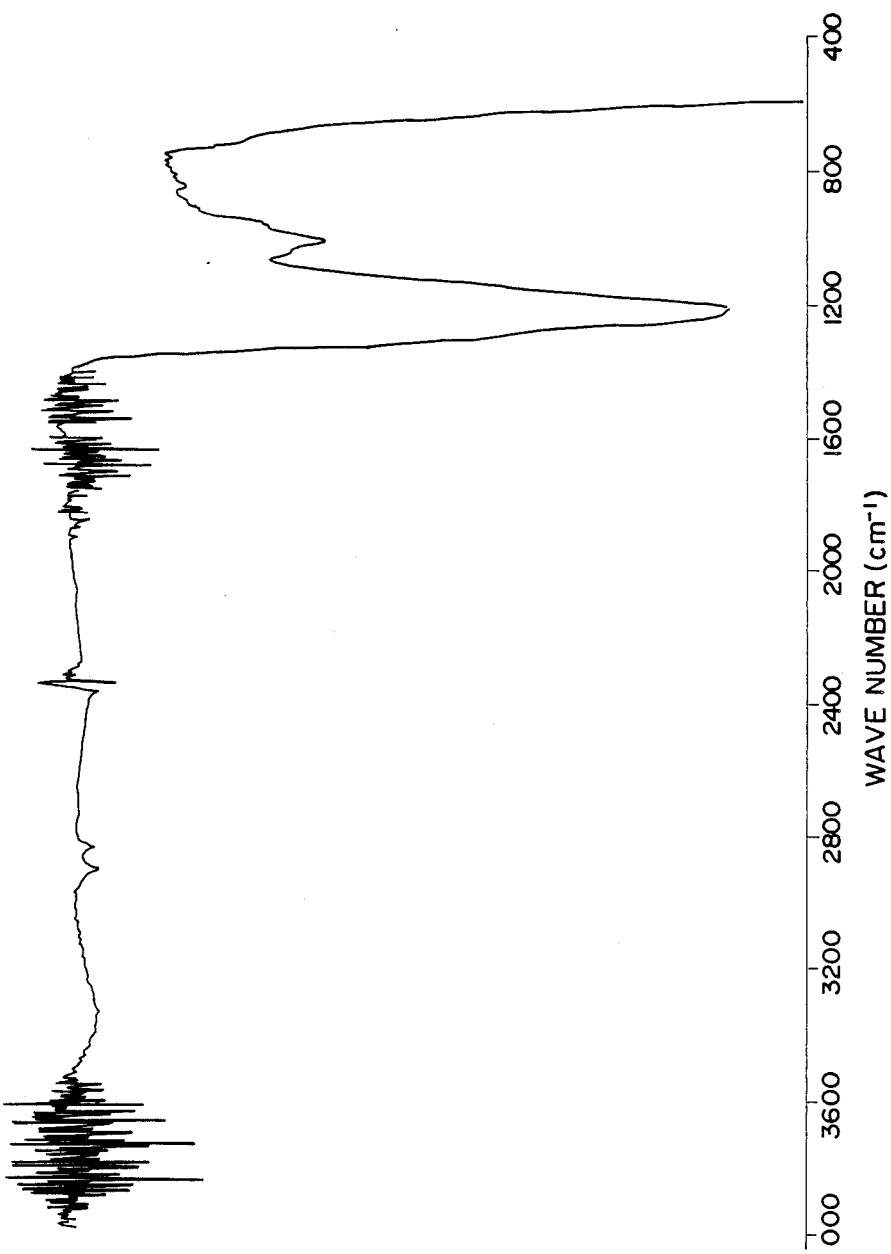
FIGS. 22, 23 and 24, respectively, show the IR spectrum, TGA and DTA curves and $^{19}F$-NMR spectrum of a liquid fluorocarbon of the present invention obtained in Example 8 as described later.
Figure 23:
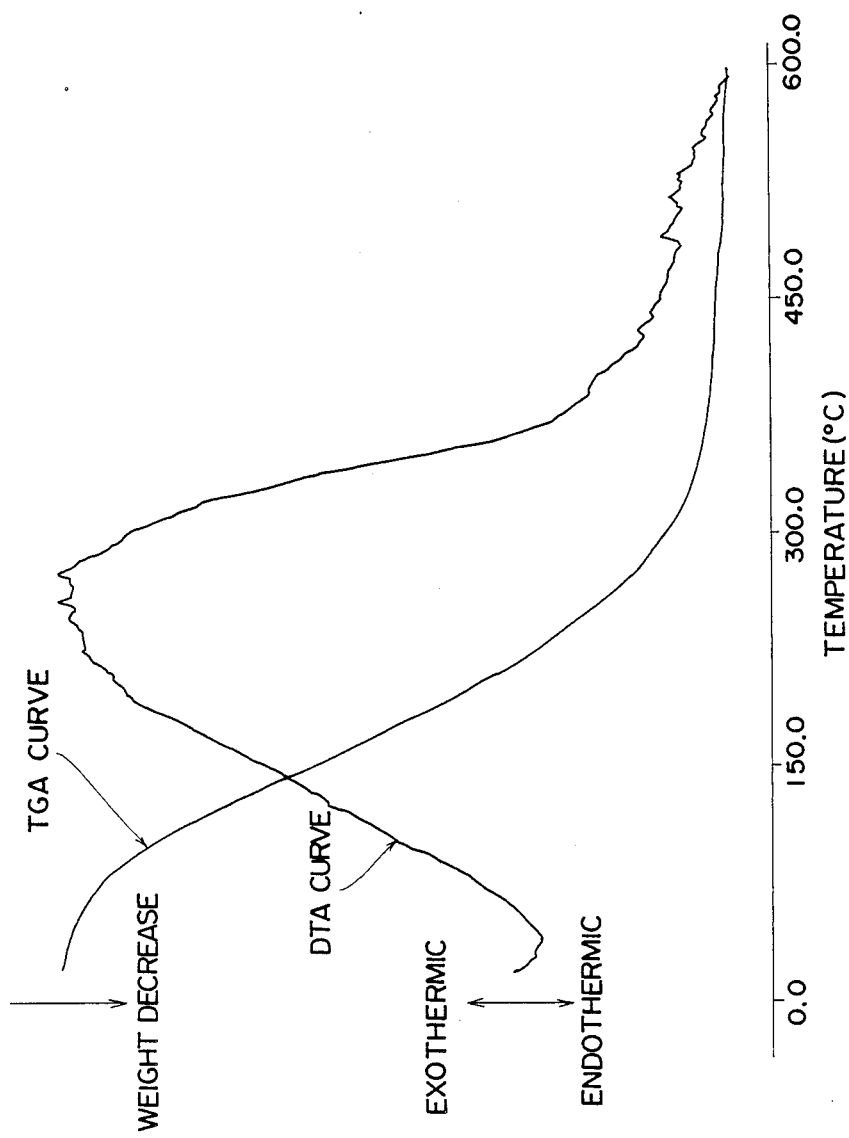
Figure 24:
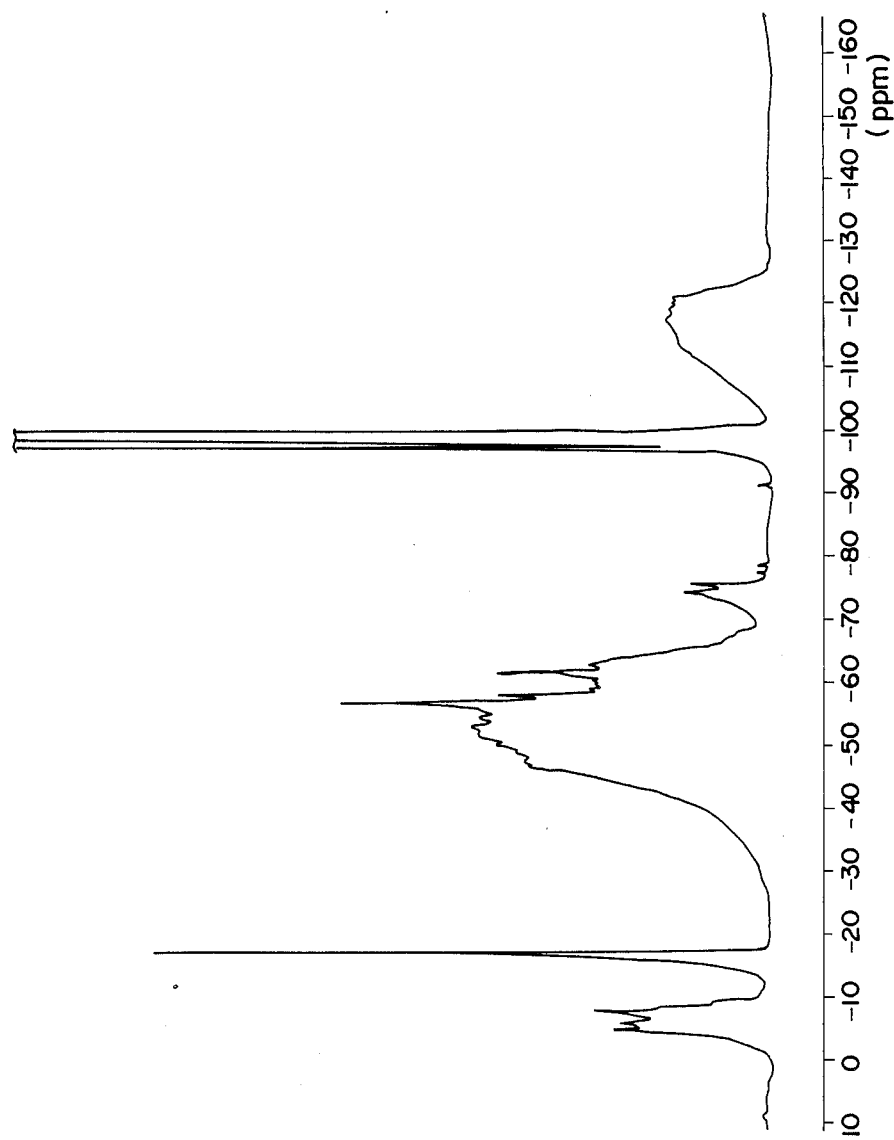

The inside of the reaction vessel was evacuated and, then, filled with an argon gas until the internal pressure thereof reached an atmospheric pressure. Thereafter, a fluorine gas was flowed into the inside of the reaction vessel at a flow rate of 6 cc/min for 10 hours while maintaining the temperature in the reaction vessel at 70° C. (first step). The temperature was elevated to 300° C. at a temperature elevation rate of 1° C./min, and this temperature was then kept for 12 hours (second step), to thereby obtain 0.41g of a liquid fluorocarbon. The F/C atomic ratio and number average molecular weight of the liquid fluorocarbon were 1.50 and 731 ±40, respectively. The IR spectrum, TGA and DTA curves and NMR spectrum of the liquid fluorocarbon are shown in FIGS. 22, 23 and 24, respectively.

What is claimed is:

1. A liquid fluorocarbon comprising carbon atoms and fluorine atoms and having no double bond, the atomic ratio of fluorine to carbon atoms being 1.50 to 1.93; the liquid fluorocarbon exhibiting:
   (a) in the infrared absorption spectrum, a peak at about 1215 ±7 cm$^{-1}$ having a maximum intensity, a peak at about 1025 ±7 cm$^{-1}$ having an intensity lower than that of said peak appearing at about 1215 ±7cm$^{-1}$ and a peak at about 971 ±7 cm$^{-1}$ having an intensity lower than that of said peak appearing at about 1025 ±7cm$^{-1}$;
   (b) a number average molecular weight of 680 to 950 as measured by the vapor pressure osmotic pressure method;
   (c) in the thermogravimetric analysis and differential thermal analysis curves, an exothermic, weight decrease with the temperature alevation up to 420° C., wherein a 100 % weight decrease is reached at 420° C.;
   (d) a liquid state at room temperature; and
   (e) in the $^{19}$F-NMR spectrum as measured taking the CF$_3$ group of benzotrifluoride as a standard for chemical shift, two peaks respectively ascribed to CF$_3$CF- and CF$_3$CF$_2$groups at chemical shifts within the range of from 0 to −30 ppm, a broad peak ascribed to a CF$_2$ group at a chemical shift within the range of from −30 to −90 ppm and a peak ascribed to a CF group at a chemical shift within the range of from −100 to −150 ppm.

2. A method for producing a liquid fluorocarbon, which comprises the steps of (1) reacting a pitch with fluorine at a reaction temperature of from about 0 to about 350° C. in a reaction zone and (2) elevating the temperature of said reaction zone containing the resultant pitch fluoride and fluorine to and then maintaining said reaction zone at a temperature which is higher than said reaction temperature but not higher than about 550° C.

3. A method according to claim 2, wherein the reaction temperature in step (1) is from about 0 to about 200° C.

4. A method according to claim 3, wherein the reaction temperature in step (1) is from about 0 to about 150° C.

5. A method for producing a liquid fluorocarbon, which comprises reacting a pitch with fluorine in an atmosphere of fluorine in a reaction zone while elevating the temperature of said reaction zone to a temperature within the range of from about 200° C. to about 550° C.

6. A method for producing a liquid fluorocarbon, which comprises heat-treating a solid pitch fluoride in an atmosphere of fluorine in a heating zone while elevating the temperature of said heating zone to a temperature which is sufficient for converting said solid pitch fluoride to a liquid fluorocarbon, with the proviso that the elevated temperature is not higher than about 550° C.

7. A method according to claim 6, wherein the elevated temperature is from about 200° C. to about 550° C.

* * * * *